United States Patent
Brooks et al.

(10) Patent No.: US 9,789,056 B2
(45) Date of Patent: *Oct. 17, 2017

(54) POLYMER-BASED SERUM ALBUMIN SUBSTITUTE

(71) Applicant: THE UNIVERSITY OF BRITISH COLUMBIA, Vancouver (CA)

(72) Inventors: Donald E. Brooks, Vancouver (CA); Jayachandran N. Kizhakkedathu, Vancouver (CA); Rajesh Kumar Kainthan, Tappan, NY (US)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,559

(22) Filed: Apr. 18, 2016

(65) Prior Publication Data

US 2017/0042804 A1    Feb. 16, 2017

Related U.S. Application Data

(63) Continuation of application No. 11/916,525, filed as application No. PCT/CA2006/000936 on Jun. 6, 2006, now Pat. No. 9,346,029.

(60) Provisional application No. 60/687,336, filed on Jun. 6, 2005.

(51) Int. Cl.
| | | |
|---|---|---|
| A61K 9/00 | (2006.01) | |
| A61K 47/34 | (2017.01) | |
| A61K 47/48 | (2006.01) | |
| C08G 65/34 | (2006.01) | |
| B01F 17/00 | (2006.01) | |
| C08L 71/00 | (2006.01) | |

(52) U.S. Cl.
CPC ............ *A61K 9/0026* (2013.01); *A61K 47/34* (2013.01); *A61K 47/48215* (2013.01); *B01F 17/0021* (2013.01); *C08G 65/34* (2013.01); *C08L 71/00* (2013.01); *C08G 2650/04* (2013.01); *C08G 2650/32* (2013.01); *C08G 2650/38* (2013.01)

(58) Field of Classification Search
None
See application file for complete search history.

(56) References Cited

U.S. PATENT DOCUMENTS

| | | |
|---|---|---|
| 4,814,470 A | 3/1989 | Colin et al. |
| 5,112,876 A | 5/1992 | Tairaka et al. |
| 5,407,528 A | 4/1995 | McGrath et al. |
| 5,688,977 A | 11/1997 | Sisti et al. |
| 5,830,948 A | 11/1998 | Frechet et al. |
| 6,039,967 A | 3/2000 | Ottoboni et al. |
| 6,207,180 B1 | 3/2001 | Ottoboni et al. |
| 6,469,218 B1 | 10/2002 | Rexin et al. |
| 6,524,608 B2 | 2/2003 | Ottoboni et al. |
| 6,730,334 B2 | 5/2004 | Zhao |
| 6,765,082 B2 | 7/2004 | Sunder et al. |
| 6,822,068 B2 | 11/2004 | Sunder et al. |
| 6,838,528 B2 | 1/2005 | Zhao |
| 6,862,167 B1 | 3/2005 | Banno et al. |
| 6,894,071 B2 | 5/2005 | Nuijen et al. |
| 6,897,266 B2 | 5/2005 | Kenig-Dodiuk |
| 6,949,335 B2 | 9/2005 | Fahy et al. |
| 7,063,860 B2 | 6/2006 | Chancellor et al. |
| 7,265,186 B2 | 9/2007 | Zhao |
| 7,320,963 B2 | 1/2008 | Esuvaranathan et al. |
| 7,393,841 B2 | 7/2008 | Sommermeyer |
| 7,396,861 B2 | 7/2008 | Loccufier et al. |
| 7,550,255 B2 | 6/2009 | Fahy et al. |
| 7,550,446 B2 | 6/2009 | Henning |
| 7,709,457 B2 | 5/2010 | Esuvaranathan et al. |
| 7,875,698 B2 | 1/2011 | Vanmaele et al. |
| 7,977,369 B2 | 7/2011 | Nuijen et al. |
| 8,354,549 B2 | 1/2013 | Zhang |
| 8,519,189 B2 | 8/2013 | Kizhakkedathu et al. |
| 8,637,008 B2 | 1/2014 | Kizhakkedathu et al. |
| 9,186,410 B2 | 11/2015 | Burt et al. |
| 9,346,029 B2 | 5/2016 | Brooks et al. |
| 2005/0042293 A1 | 2/2005 | Jackson et al. |
| 2006/0127420 A1 | 6/2006 | Chung et al. |
| 2008/0108693 A1 | 5/2008 | Liao et al. |
| 2008/0292579 A1 | 11/2008 | Brooks et al. |
| 2009/0105351 A1 | 4/2009 | Jackson et al. |
| 2010/0324150 A1 | 12/2010 | Allard et al. |
| 2011/0060036 A1 | 3/2011 | Nie et al. |

(Continued)

FOREIGN PATENT DOCUMENTS

| | | |
|---|---|---|
| JP | 2007503514 | 2/2007 |
| WO | 0077070 | 12/2000 |
| WO | 2005028539 | 3/2005 |

(Continued)

OTHER PUBLICATIONS

"SEC Analysis of Polymers with Light Scattering Detection," (2004) G.I.T. Laboratory Journal, 2-5.

(Continued)

*Primary Examiner* — Susan Tran
*Assistant Examiner* — William Craigo
(74) *Attorney, Agent, or Firm* — Rudy J. Ng; Carol L. Francis; Bozicevic, Field & Francis LLP

(57) ABSTRACT

This invention provides the use of a polymer comprising a hyperbranched polyether polyol such as hyperbranched polyglycerol as a serum albumin substitute. Also provided are high molecular weight hyperbranched polyglycerol polymers suitable for a variety of medical and non-medical uses including methods for making such high molecular weight polymers.

63 Claims, No Drawings

(56) References Cited

U.S. PATENT DOCUMENTS

| | | | |
|---|---|---|---|
| 2014/0127312 A1 | 5/2014 | Kizhakkedathu et al. | |
| 2016/0114040 A1 | 4/2016 | Burt et al. | |

FOREIGN PATENT DOCUMENTS

| | | |
|---|---|---|
| WO | 2005037911 | 4/2005 |
| WO | 2005079856 | 9/2005 |
| WO | 2006130978 | 12/2006 |
| WO | 2008066902 | 6/2008 |
| WO | 2008074154 | 6/2008 |
| WO | 2008123751 | 10/2008 |
| WO | 2009055935 | 7/2009 |
| WO | 2009141170 | 11/2009 |
| WO | 2012031245 | 5/2012 |
| WO | 2012162789 | 12/2012 |
| WO | 2013159188 | 10/2013 |

OTHER PUBLICATIONS

Chen (2006) "Synthesis of Multarm Star Poly(glycerol)-block-Poly(2-hydroxyethyl methacrylate)," Biomacromolecules, 7: 919-926.

Dworak et al., (1995) "Cationic polymerization of glycidol. Polymer Structure and polymerization mechanism," Macromol. Chem. Phys., 196:1963-1970.

Go et al. (2001) "Comparative Pharmacology and Clinical Activity of Cisplatin and Carboplatin," Oncolink-Abramson Cancer of University of Pennsylvania: 1-3.

Kautz et al. (2001) "Control of the Molecular Weight of Hyperbranched Polyglycerols," Macromol. Symp. 163:67-73.

Tokar et al., (1994) "Cationic Polymerization of Glycidol: Coexistence of the Activated Monomer and Active Chain End Mechanism," Macromolecules, 27:320-322.

Zhang et al. (1996) "Development of amphiphilic diblock copolymers as micellar carriers of taxol," International J. Pharmaceutics, 132: 195-206.

Mugabe et al. (2012) "Enhanced tissue uptake of docetaxel loaded hydrophobically derivatized hyperbranched polyglycerols and their effects on the morphology of the bladder urothelium," Abstract, 27th Annual Congress of the European Association of Urology, Feb. 24-28, 2012.

Mugabe et al. (2012) "Tissue uptake of docetaxel loaded hydrophobically derivatized hyperbranched polyglycerols and their effects on the morphology of the bladder urothelium," Biomaterials, 33(2): 692-703. Epub Oct. 19, 2011.

Mugabe et al. (2013)"Tolerability and Pharmacokinetic Properties of Intravesical Docetaxel Loaded Amine Terminated Hyperbranched Polyglycerol Nanoparticles,"SIU Academy, Sep. 9, 2013.

Ooya (2004) "Hydrotropic Dendrimers of Generations 4 and 5: Synthesis, Characterization, and Hydrotropic Solubilization of Paclitaxel," Bioconjugate Chem, 15: 1221-1229.

Ooya (2005) "Self-assembly of cholesterol-hydrotropic dendrimer conjugates into micelle-like structure: Prepartion and hydrotropic solubilisation of paclitaxel," Science and Technology of Advanced Materials, 6: 452-456.

Panyam (2002) "Rapid endo-lysosomal escape of poly(DL-lactide-co-glycolide) nanoparticles: implications for drug and gene delivery," FASEB J., 16: 1217-1226.

Reichert (2011) "Size-dependant cellular uptake of dendritic polyglycerol," 7(6): 820-829. Epub Feb. 18, 2011.

Rosato (2006) "HYTADI-p20: A new paclitaxel-hyaluronic acid hydrosoluble bioconjugate for treatment of superficial bladder cancer," Urologic Oncology: Seminars and Original Investigations. 24: 207-215.

Rossi et al. (2010) "Enhanced cell surface polymer grafting in concentrated and nonreactive aqueous polymer solutions," J Am Chem Soc. 17, 132(10): 3423-3430.

Rossi et al. (2010) "Red blood cell membrane grafting of multifunctional hyperbranched polyglycerols." Biomaterials. 31(14): 4167-4178. Epub Feb 20, 2010.

Seiler (2006) "Hyperbranched Polymers: Phase behavior and new applications in the field of chemical engineering," Fluid Phase Equilibria, 241: 155-174.

Shelley (2010) "Intravesical Therapy for Superficial Bladder Cancer: A systematic Review of Randomised Trials and Meta-Analyses," Cancer Treatment Reviews,36: 195-205.

Shen (2008) "Intravesical Treatments of Bladder Cancer: Review," Pharmaceutical Research, 25(7): 1500-1510.

Shenoy (2005) "Poly(Ethylene Oxide)-Modified Poly(β-amino Ester) Nanoparticles as a pH-Sensitive System for Tumor-Targeted Delivery of Hydrophobic Drugs: Part I. In vitro Evaluations," Mol Pharm, 2(5): 357-366.

Smart (2005) "The basics and underlying mechanisms of mucoadhesian," Advanced Drug Delivery Reviews, 57: 1556-1568.

Sogias (2008) "Why is Chitosan Mucoadhesive," Macromolecules, 9(7): 1837-1842.

Song et al (1997) "Bladder Tissue Pharmacokinetics of Intravesical Taxol," Cancer Chemother Pharmacol, 40(4): 285-292.

Sparreboom (2005) "Comparative Preclinical and Clinical Pharmacokinestics of a Cremophor-Free, Nanoparticle Albumin-Bound Paclitaxel (ABI-007) and Paclitaxel Formulated in Cremophor (Taxol)," Clin Cancer Res, 11: 4136-4143.

Sternberg (2013) "ICUD-EAU International Consultation on Bladder Cancer 2012: Chemotherapy for Urothelial Carcinoma—Neoadjuvant and Adjuvant Settings," European Urology, 63: 58-66.

Vicari et al. (2008) "Paciltaxel loading in PLGA nanospheres affected the in vitro drug cell accumulation and antiproliferative activity," BMC Cancer., 8: 212.

Wilms (2010) "Hyperbranched Polyglycerols: From the controlled Synthesis of Biocompatible Polyether Polyols to Multipurpose Applications," Accounts of Chemical Research, 43(1): 129-141.

Wosnitzer et al. (2012) "A Comparison of the Outcomes of Neoadjuvant and Adjuvant Chemotherapy for Clinical T2-T4 a N0-N2 MO Bladder Cancer," Cancer, 2012 118(2): 358-364.

Xiao (2003) "Whole bladder photodynamic therapy for orthotopic superficial bladder cancer in rats: a study of intravenous and intravesical administration of photosensitizers," J Urol., 169: 352-356.

Yan and Muller (1997) "Molecular Parameters of Hyperbranched Polymers Made by Self-condensing Vinyl Polymerization. 2. Degree of Branching," Macromolecules., 30: 7024-7033.

Yeh et al. (2008) "Self-assembled monothiol-terminated hyperbranched polyglycerols on a gold surface: a comparative study on the structure, morphology, and protein adsorption characteristics with linear poly(ethylene glycol)s," Langmuir., 24(9): 4907-16. Epub Mar 25, 2008.

Zapatero (2012) "Long-Term Results of Two Prospective Bladder-sparing Trimodality Approaches for Invasive Bladder Cancer: neoadjuvant Chemotherapy and Concurrent Radio-chemotherapy," Urology., 80: 1056-1062.

Zhang et al. (2008) "Conjugation to hyperbranched polyglycerols improves RGD-mediated inhibition of platelet function in vitro," Bioconjug Chem., 19(6): 1241-7. Epub May 14, 2008.

Zhigaltsev (2010) "Development of a weak-base docetaxel derivatives that can be loaded into lipid nanoparticles," J. Control Release., 144(3): 332-340.

Giannantoni (2006) "New Frontiers in Intravesical Therapies and Drug Delivery," European Urology. 50: 1183-1193.

Knischaka & Lutz (2000) "Funtional Poly(ethylene oxide) Multiarm Star Polymers: Core-First Synthesis Using Hyperbranched Polyglycerol Initiators" Macromolecules, 33:315-320. cted in ISR in PCT/2006/130978 dtd Oct. 5, 2006.

Ofek et al. (2010) "In Vivo Delivery of Smal Interfering RNA to Tumors and Their Vasculature by Novel Dendritic Nanocarriers" FASEB J 2415(9):3122-3231.

Tziveleka et al. (2008) "Synthesis and Evaluation of Functional Hyperbranched Polyether Polyols as Prospected Gene Carriers" Int J Pharm 356(1-2)314-324.

(56) References Cited

OTHER PUBLICATIONS

Abbo et al. (2010) "Phase I clinical trial and pharmacokinetics of intravesical mitomycin C in dogs with localized transitional cell carcinoma of the urinary bladder." J Vet Intern Med, 24(5):1124-30.
Arentsen et al. (2011) "Pharmacokinetics and toxicity of intravesical TMX-101: a preclinical study in pigs." BJU Int, 108(7): 1210-1214.
Barthelmes et al. (2011) "Development of a mucoadhesive nanoparticulate drug delivery system for a targeted drug release in the bladder." Int J Pharm, 416 (1): 339-345.
Chang et al. (2009) "Optimization of epirubicin nanoparticles using experimental design for enhanced intravesical irug delivery." Int J Pharm, 376(1-2): 195-203.
Cho (1992) "Adriamycin absorption after Nd:YAG laser coagulation compared to electrosurgical resection of the bladder wall," J Urol, 147(4):1139-1141.
Dalmose et al. (2000) "Surgically induced urologic models in swine." J Invest Surg, 13(3): 133-145.
Di Stasi et al. (1997) "Electromotive administration of oxybutynin into the human bladder wall." J Urol, 158(1): 228-233.
Di Stasi et al. (1997) "Electromotive delivery of mitomycin C into human bladder wall." Cancer Res, 57(5): 875-880.
Di Stasi et al. (2003) "The stability of lidocaine and epinephrine solutions exposed to electric current and comparative administration rates of the two drugs into pig bladder wall." Urol Res, 31(3): 169-176.
Dumey et al. (2005) "In vivo retroviral mediated gene transfer into bladder urothelium results in preferential transduction of tumoral cells." Eur Urol, 47(2): 257-263.
Gontero et al. (2010) "Pharmacokinetic study to optimize the intravesical administration of gemcitabine." BJU Int, 106(11): 1652-1656.
Hara (1989)"Fundamental studies on intravesical instillation of interferons in the treatment of bladder cancer." Nihon Hinyokika Gakkai Zasshi, 80(2): 158-166.
Hirao et al. (1985) "Fundamental studies on intravesical instillation of cis-diamminedichloroplatinum for treatment of urinary bladder tumors. I: On the effects of intravesical instillation of cis-diamminedichloroplatinum in normal beagle dogs," Hinyokika Kiyo, 31(1): 31-38.
Matsumura et al. (1983) "Intravesical adriamycin chemotherapy in bladder cancer". Cancer Chemother Pharmacol, 11: 69-73.
Mross et al. (1992) "Tissue disposition and plasma concentrations of idarubicin after intravesical therapy in patients with bladder tumors." Cancer Chemother Pharmacol, 29(6): 490-494.
Ohmori et al. (1996) "Experimental studies on intravesical instillation of SM-5887, a novel anthracycline derivative for treatment of bladder carcinoma," Gan To Kagaku Ryoho, 23(5): 601-606.
Song et al. (1997)"Bladder tissue pharmacokinetics and antitumor effect of intravesical 5-fluorouridine." Clin Cancer Res, 3(6): 901-909.
Tsushima (1985) "Fundamental studies on intravesical instillation of 4'-epi-adriamycin for the treatment of bladder cancer." Hinyokika Kiyo, 31(11): 1945-1956.
Van Staveren et al. (2002) "Comparison of normal piglet bladder damage after PDT with oral or intravesical administration of ALA." Lasers Med Sci, 17(4): 238-245.
Wientjes et al. (1996) "M.G., Badalament, R.A., and Au, J.L., Penetration of Intravesical Doxorubicin in Human Bladders." Cancer Chemother Pharmacol, 37(6): 539-546.
Witjes et al. (2003) "Pharmacokinetics of intravesical gemcitabine: a preclinical study in pigs." Eur Urol, 44(5): 615-619.
Ahn & McKiernan (2013) "New Agents for Bacillus Calmette-Guerin-Refactory Bladder Cancer," Urol Clin N Am.:1-14.
Andrews (2009) "Mucoadhesive polymeric platforms for controlled drug delivery," European journal of pharmaceutics and biopharmaceutics : official journal of Arbeitsgemeinschaft fur Pharmazeutische Verfahrenstechnik e.C., 71(3): 505-518.

Au (2001) "Methods to Improve Efficacy of Intravesical Mitomycin C: Results of a Randomized Phase III Trial," J Natl Cancer Inst, 18;93(8):597-604.
Barlow (2013) "Experience with Newer Intravesical Chemotherapy for High-Risk Non-Muscle-Invasive Bladder Cancer," Curr Urol Rep, 14: 65-70.
Barlow (2013) "Long Term Survival Outcomes with Intravesical Docetaxel for Recurrent Nonmuscle Invasive Bladder Cancer After Previous Bacillus Calmette-Guerin Therapy," The Journal of Urology, 189: 834-839.
Bassi (2011) "Paclitaxel-Hyaluronic Acid for Intravesical Therapy of Bacillus Calmette-Guerin Refactory Carcinoma In-Situ of the Bladder Cancer: Results of a Phase I Study," The Journal of Urology, 85: 445-449.
Bélanger & Marois (2001) "Hemocompatibility, Biocompatibility, Inflammatory and in Vivo Studies of Primary Reference Materials Low-Density Polyethylene and Polydimethylsiloxane: A Review," J.Biomed Mater Res (Appl Biomater) 58(5): 467-477. Epub Jul. 5, 2001.
Burjak et al. (2001) "The study of drug release from microspheres adhered on pig vesical mucosa." Int J Pharmaceutics, 224(1-2):123-130.
Chen et al. (2003) "Effect of Dimethyl Sulfoxide on Bladder Tissue Penetration of Intravesical Paclitaxel," Clinical Cancer Res, 9(1): 363-369.
Elsasser-Beile et al. (2005) "Adjuvant Intravesical Treatment of Superficial Bladder Cancer with a Standardized Mestletoe Extract," The Journal of Urology, 174: 76-79.
Eroglu (2002) "Design and evaluation of a mucoadhesive therapeutics agent delivery system for postoperative chemotherapy in superficial bladder cancer," International Journal of Pharmaceutics, 235: 51-59.
Fefelova (2007) "Mucoadhesive interactions of amphiphilic cationic copolymers based on [2-(methacryloyloxy)ethyl] trimethylammonnium chloride," International Journal of Pharmaceutics. 339, 25-32.
Frey (1999) "Degree of branching in hyperbranched polymepolymers. 3 copolymerization of Abm-monomers with AB and Abn-monomers," Acta Polymerica. 50 (203): 67-76.
Gaison (2006) "Improving Efficacy of Intravesical Chemotherapy," European Urology. 50: 225-234.
Gong (2007) "In vitro and in vivo degradability and cytocompatibility of poly(L-lactic acid) scaffold fabricated by gelatin particle leaching method," Acta Biomaterialia. 3: 531-540.
Hall (2007) "Chapter 1: The Management of Bladder Cancer: Diagnosis and Treatment Recommendations (Guidelines for the Management of Nonmuscle Invasive Bladder Cancer: (Stages TA, T1 and TIS: Update," The Journal of Urology, 178:2314-2330.
Hasselmann (1998) "Hyperbranched Polymers Prepared via the Core-Dilutions/Slow Addition Techniques: Computer Simulation of Molecular Weight Distribution and Degree of Branching," Macromolecules. 31: 3790-3801.
Haxton & Burt (2009) "Polymeric drug delivery of platinum-based anticancer agents," J Pharm Sci. 98(7): 2299-2316. Epub Nov. 13, 2008.
Hennenfent (2006) "Novel Formulations of Taxanes: a review. Old wine in a new bottle," Annals of Oncology, 17: 735-749.
Highley (1999) "Intravesical Drug Delivery Pharmacokinetic and Clinical Consideration," Clin Pharmacokinet, 3(1): 59-73.
Hölter (1997) "Degree of branching in hyperbranched polymers," Acta Polymer, 48: 30-35.
Hreczuk-Hirst (2001) "Dextrins as potential carriers for drug targeting: tailored rates of dextrin degradation by introduction of pendant groups," International Journal of Pharaceutics, 230: 57-66.
Kainthan & Brooks (2007) "In vivo biological evaluation of high molecular weight hyperbranched polyglycerols," Biomaterials, 28(32): 4779-4787. Epub Aug. 15, 2007.
Kainthan et al. (2006) "Biocompatibility Testing of Branched and Linear Polyglycidol," Biomacromolecules, 7(3): 703-709.
Kainthan et al. (2006) "Blood compatibility of novel water soluble hyperbranched polyglycerol-based multivalent cationic polymers and their interaction with DNA," Biomaterials, 27(31): 5377-5390. Epub Jul. 18, 2006.

(56) References Cited

OTHER PUBLICATIONS

Kainthan et al. (2006) "Synthesis, Characterization, and Viscoelastic Properties of High Molecular Weight Hyperbranched Polyglycerols," Macromolecules, 31;39(22): 7708-7717.

Kainthan et al. (2007) "In Vitro biological evaluation of high molecular weight hyperbranched polyglycerols," Biomaterials, 28(3): 4581-4590. Epub Aug. 3, 2007.

Kala (2014) "Combination of Dendrimer-nanovector-Medicated Small Interfereing RNA Delivery to Target Akt with the Clinical Anticancer Drug Paclitaxel for Effective and Potent Anticancer Activity in Treating Ovarian Cancer," J. Med. Chem., 57(6): 2634-2642.

Kerec (2005) "Permeability of Pig Urinary Bladder Wall: the effect of chitosan and the role of calcium," European of Pharmaceutical sciences, 25: 113-121.

Kerec (2006) "Permeability of Pig Urinary Bladder Wall: Time and Concentration Dependent Effect of Chitosan," Biol. Pharm. Bull., 29(8) 1685-1691.

Kerec et al. (2009) "Enhanced permeability of the urinary bladder wall; the role of polymer charge," Pharmazie, 64(4): 232-237.

Khan et al. (2006) "Water soluble nanoparticles from PEG-based cationic hyperbranched polymer and RNA that protect RNA from enzymatic degradation," Biomacromolecules, 7(5): 1386-1388. Epub Apr. 8, 2006.

Kizhakkedathu et al. (2010) "High molecular weight polyglycerol-based multivalent mannose conjugates," Biomacromolecules, 11(10): 2567-2575.

Knemeyer et al. (1999) "Cremophor reduces paclitaxel penetration into bladder wall during intravesical treatment," Cancer Chemother Pharmacol, 44 (3): 241-248.

Knuchel (1989) "Sensitivities of Monolayers and Spheroids of the Human Bladder Cancer Cell LIne MGH-U1 to the Drugs Used for Intravesical Chemotherapy," Cancer Research, 49: 1397-1401.

Koç et al. (2005) "Highly Regioselective Synthesis of Amino-Functionalized Dendritic Polyglycerols by a One-Pot Hydroformylation/Reductive Amination Series," J Org Chem, 70(6): 2021-2025. Epub Feb. 16, 2005.

Kolishetti (2010) "Engineering of self-assembled nanoparticle platform for precisely controlled combination drug therapy," PNAS. 107(42): 17939-17944.

Kumar et al. (2004) "Atom Transfer Radical Polymerization using multidentate amine ligands supported on soluble hyperbranched polyglycidol," Macromol Chem Phys, 205(5): 567-573.

Le Visage (2004) "Efficacy of Paclitaxel Released from Bio-Adhesice Polymer Microspheres on Model Superficial Bladder Cancer," The Journal of Urology, 171: 1324-1329.

Leakakos et al. (2003) "Intravesical administration of doxorubicin to swine bladder using magnetically targeted carriers," Cancer Chemother Pharmacol, 51(6): 445-450.

Lee (2005) "Designing Dendrimers for Biological Applications," Nature Biotechnology, 23(12).

Lee et al. (2005) "Bioadhesive drug delivery system using glyceryl monooleate for the intravesical administration of paclitaxel," Chemotherapy, 51(6): 311-318.

Liu et al. (2010) "Adsorption of amphiphilic hyperbranched polyglycerol derivatives onto human red blood cells," Biomaterials, 31(12): 3364-73. Epub Feb. 1, 2010.

Lu et al. (2004) "Paclitaxel Gelatin Nanoparticles for Intravesical Bladder Cancer Therapy," Clinical Cancer Res., 10 (22): 7677-7684.

Lu et al. (2011) "Paclitaxel Gelatin Nanoparticles for Intravesical Bladder Cancer Therapy," J Urol, 185(4): 1478-1483.

Luo (2002) "Cellular Internalization of Poly(ethylene oxide)-b-poly-(ε-caprolactone) Diblock Copolymer Micelles," Bioconjugate Chem, 13: 1259-1265.

McKiernan (2011) "A Phase I Trial of Intravesical Nanoparticle Albumin-Bound Paclitaxel in the Treatment of Bacillus Calmette-Guerin Refactory Nonmuscle Invasive Bladder Cancer," The Journal of Urology, 186: 448-451.

McKiernan "Updated Results of the Combined Phase I/II Trial of Intravesical Nanoparticle Albumin-bound Paclitaxel in the Treatment of BCG Refractory Non-muscle Invasive Transitional Cell Carcinoma," Bladder Cancer: Superficial II, AUA Annual Meeting, 2012. http://www.aua2012.org/abstracts/printpdf.cfm?ID=1769.

Meng (2006) "Uptake and metabolism of novel biodegradable poly(glycerol-adipate) nanoparticles in DAOY monolayer," Journal of Controlled Release, 116: 314-321.

Mugabe et al. (2008) "Paclitaxel incorporated in hydrophobically derivatized hyperbranched polyglycerols for intravesical bladder cancer therapy," BJU International, 103(7): 978-986. Epub Oct. 31, 2008.

Brooks & Keevil (1997) "A simple artificial urine for the growth of urinary pathogens," Lett. Appl. Microbiol. 24(3):203-206.

Dalbagni (2007) "The management of superficial bladder cancer," Nat. Clin. Pract. Urol. 4(5):254-260.

Dordunoo & Burt (1996) "Solubility and Stability of Taxol: Effects of Buffers and Cyclodextrins," Int. J. Pharm. 133 (1-2)191-201.

Du et al. (2007) "Synthesis and evaluation of water-soluble docetaxel prodrugs-docetaxel esters of malic acid," Bioorg. Med. Chem. 15(18):6323-6330.

Fischer et al. (2010) "Hyperbranched Polyamines for Transfection," Top Curr Chem 296: 95-129.

Gao & Yan (2004) "Hyperbranched Polymers: From Synthesis to Applications," Prog. Polym Sci. 29:183-275.

Grabnar et al. (2003) "Influence of chitosan and polycarbophil on permeation of a model hydrophilic drug into the urinary bladder wall," Int J Pharm 256(1-2):167-173.

Haag et al. (2000) "An Approach to Core-Shell-Type Architectures in Hyperbranched Polyglycerols by Selective Chemical Differentiation," Macromolecules 33(22):8158-8166.

Haag et al. (2002) "Dendritic aliphatic polyethers as high-loading soluble supports for carbonyl compounds and parallel membrane separation techniques," J. Comb. Chem. 4(2):112-119.

Hadaschik et al. (2007) "A validated mouse model for orthotopic bladder cancer using transurethral tumour inoculation and bioluminescence imaging," BJU Int. 100(6):1377-1384.

Hadaschik et al. (2008) "Intravesical chemotherapy of high-grade bladder cancer with HTI-286, a synthetic analogue of the marine sponge product hemiasterlin," Clin Cancer Res. 14(5)1510-1518.

Hadaschik et al. (2008) "Oncolytic vesicular stomatitis viruses are potent agents for intravesical treatment of high-risk bladder cancer," Cancer Res. 68(12)4506-4510.

Hadaschik et al. (2008) "Paclitaxel and cisplatin as intravesical agents against non-muscle-invasive bladder cancer," BJU Int. 101(11):1347-1355.

Haxton & Burt (2008) "Hyperbranched polymers for controlled release of cisplatin," Dalton Trans.(43):5872-5875. Epub Sep. 25, 2008.

Henni et al. (2007) "Enhancement of the solubility and efficacy of poorly water-soluble drugs by hydrophobically-modified polysaccharide derivatives," Pharm Res 24(12):2317-2326.

Huang et al. (2003) "Involvement of endocytic organelles in the subcellular trafficking and localization of riboflavin," J. Pharmacol. Exp. Ther. 306(2):681-687.

Iwase et al. (2004) "Cremophor EL Augments the Cytotoxicity of Hydrogen Peroxide in Lymphocytes Dissociated from Rat Thymus Glands," Toxicol Lett, 154(1-2) 143-148.

Jackson et al. (2004) "Characterization of perivascular poly(lactic-co-glycolic acid) films containing paclitaxel," Int. J. Pharma. 283(1-2):97-109.

Jasti et al. (2003) "Recent advances in Mucoadhesive Drug Delivery Systems," Business Briefing Pharmatech 194-196.

Kainthan & Brooks (2008) "Unimolecular micelles based on hydrophobically derivatized hyperbranched Polyglycerols: biodistribution studies," Bioconjugate Chemistry, 19(11):2231-2238. Epub Oct. 11, 2008.

Kainthan et al. (2008) "Hydrophobically derivatized hyperbranched polyglycerol as a human serum albumin substitute," Biomaterials, 29(11):1693-1704. Epub Jan. 14, 2008 Epub Oct. 11, 2008.

(56) References Cited

OTHER PUBLICATIONS

Kainthan et al. (2008) "Unimolecular micelles based on hydrophobically derivatized hyperbranched polyglycerols: ligand binding properties," Biomacromolecules 9(3):886-895. Epub Feb. 2, 2008.
Karger-Kocsis et al. (2004) "Synthesis of Reactive Hyperbranched and Star-Like Polyethers and their use for toughening of Vinylester-Urethane Hybrid Resins," Polymer, 45:1185-1195.
<Khandare et al. (2010) "Structure-biocompatibility relationship of dendritic polyglycerol derivatives," Biomaterials 31(15): 4268-4277.
Liggins et al. (1997) "Solid-state characterization of paclitaxel," Pharm. Sci. 86(12):1458-1463.
Meise (2009) "Modular Synthesis of Hyperbranched Polyglycerol Supported N-Heterocyclic Carbene Ligands for Application in Catalysis," Freie Universitat Berlin, Dissertation. 150 pages.
Mugabe et al. (2011) "Development and in vitro characterization of paclitaxel and docetaxel loaded into hydrophobically derivatized hyperbranched polyglycerols," Int J. Pharm. 404(1-2):238-249. Epub Nov. 17, 2010.
Mugabe et al. (2011) "In vitro and in vivo evaluation of intravesical docetaxel loaded hydrophobically derivatized hyperbranched polyglycerols in an orthotopic model of bladder cancer," Biomacromolecules 12(4):949-960. Epub Mar. 1, 2011.
Mugabe et al. (2011) "In vivo efficacy of intravesical paclitaxel and docetaxel loaded hydrophobically derivatized hyperbranched polyglycerols," Nanomedicine in press DOI: 10.2217NNM.11. 37 pages.
Mugabe et al. (2011) "In vivo evaluation of mucoadhesive nanoparticulate docetaxel for intravesicl treatment of non-muscle-invasive bladder cancer," Clin Cancer Res. 17(9): 2788-2798. Epub Feb. 28, 2011.
Roller et al. (2005) "High-loading polyglycerol supported reagents for Mitsunobu- and acylation-reactions and other useful polyglycerol derivatives," Mol Divers 9(4):305-316.
Savic et al. (2003) "Micellar nanocontainers distribute to defined cytoplasmic organe," Science 300(5619):615-618.
Sunder et al. (1999) "Controlled Synthesis of Hyperbranched Polyglycerols by Ring-Opening Multibranching Polymerization," Macromolecules, 32(13):4240-4246.
Sunder et al. (1999) "Molecular Nanocapsules Based on Amphiphilic Hyperbranched Polyglycerols," Angew. Chem. Int. Ed. Engl. 38(23):3552-3555.
Sunder et al. (2000) "Hyperbranched Polyether Polyols: A Modular Approach to Complex Polymer Architectures," Adv. Mater . 12(3):235-239.
Sunder et al. (2000) "Hyperbranched Polyether-Polyols Based on Polyglycerol: Polarity Design by Block Copolymerization with Propylene Oxide," Macromolecule.s 33(2):309-314.
Sunder et al. (2000) "Synthesis and Thermal Behavior of Esterified Aliphatic Hyperbranched Polyether Polyols," Macromolecules. 33(4):1330-1337.
Thongborisute & Takeuchi (2008) "Evaluation of mucoadhesiveness of polymers by BIACORE method and mucin-particle method," Int. J. Pharm. 354(1-2):204-209.
Tian & Stella (2010) "Degradation of paclitaxel and related compounds in aqueous solutions III: Degradation under acidic pH conditions and overall kine," J. Pharm. Sci. 99(3):1288-1298.
Tsallas et al. (2011) "The uptake of paclitaxel and docetaxel into ex vivo porcine bladder tissue from polymeric micelle formulations," Cancer Chemother Pharmacol. 68(2):431-444.
Tziveleka et al. (2006) "Novel functional hyperbranched polyether polyols as prospective drug delivery systems," Macromol. Biosci. 6(2):161-169.
Wang et al. (2008) "Current Patents of Dendrimers and Hyperbranched Polymers in Membranes," Recent Patents on Chemical Engineering 1(1):41-51.
Ye et al. (2011) "Synthesis and Characterization of Carboxylic Acid Conjugated, Hydrophobically Derivatized, Hyperbranched Polyglycerols as Nanoparticulate Drug Carriers for Cisplatin," Biomacromolecules 12(1):145-155. Epub 2010.
Yeh et al. (2010) "A silicone-based microfluidic chip grafted with carboxyl functionalized hyperbranched polyglycerols or selective protein capture," Microfluid Nanofluid 9:199-209.
Ali et al. (1995) "Novel cytotoxic 3'-(tert-butyl) 3'-dephenyl analogs of paclitaxel and docetaxel." Journal of medicinal chemistry 38(19): 3821-3828.
Bissery et al. (1991) "Experimental antitumor activity of taxotere (RP 56976, NSC 628503), a taxol analogue." Cancer Res, 51(18): 4845-4852.
Bissery et al. (1995) "Docetaxel (Taxotere): a review of preclinical and clinical experience. Part I: Preclinical experience," Anticancer Drugs, 6(3):339-355, 363-368.
Center for Drug Evaluation and Research. Application No. NDA 20-592 Pharmacology Review(s)—Part 1. Division of Oncology Drug Products, HFD-150, Review and Evaluation of Pharmacology and Toxicology Data 1998 [cited Nov. 26, 2014]; Available from: http://www.accessdata.fda.gov/drugsatfda_docs/nda/98/20892_phrmr_P1.pdf.
Center for Drug Evaluation and Research. Application No. NDA 20-892 Pharmacology Review(s)—Part 2. Division of Oncology Drug Products, HFD-150, Review and Evaluation of Pharmacology and Toxicology Data 1998 [cited Nov. 26, 2014]; Available from: http://www.accessdata.fda.gov/drugsatfda_docs/nda/98/20892_phrmr_P2.pdf.
Cozzi et al. (1999) "Toxicology and pharmacokinetics of intravesical gemcitabine: a preclinical study in dogs" Clin Cancer Res, 5(9): 2629-2637.
Dalton et al. (1999) "Pharmacokinetics of aminolevulinic acid after intravesical administration to dogs." Pharm Res, 16(2): 288-295.
Debrdyne et al. (1985) "Intravesical and intradermal BCG-RIVM application: a toxicity study," Prog Clin Biol Res, 185B: 151-159.
Dumontet & Sikic (1999) "Mechanisms of action of and resistance to antitubulin agents: microtubule dynamics, drug transport, and cell death," J Clin Oncol, 17(3): 1061-1070.
Gao et al. (1998) "Bladder tissue uptake of mitomycin C during intravesical therapy is linear with drug concentration in urine," Clin Cancer Res, 3(1): 139-143.
Haldar et al. (1997) "Bcl2 is the guardian of microtubule integrity," Cancer Res, 57 (2):229-233.
Laudano et al. (2010) "Long-term clinical outcomes of a phase I trial of intravesical docetaxel in the management of non-muscle-invasive bladder cancer refractory to standard intravesical therapy," Urology, 75(1):134-137.
Lee et al. (2011) "Development of docetaxel-loaded intravenous formulation, Nanoxel-PM using polymer-based delivery system," J Control Release, 155(2): 262-271.
Malleswara et al. (2010) "Evaluation of the pharmaceutical quality of docetaxel injection using new stability indicating chromatographic methods for assay and impurities," Sci Pharm, 7 (2): 215-231.
Mauroy et al. (1999) "Study of the synergy of microwave hyperthermia/intravesical chemotherapy in the prevention of recurrences of superficial tumors of the bladder," Prog Urol, 9(1): 69-80.
McKiernan et al, (2006) "Phase I trial of intravesical docetaxel in the management of superficial bladder cancer refractory to standard intravesical therapy," J Clin Oncol, 24(19): 3075-3080.
Meijden et al. (1986) "The effects of intravesical and intradermal application of a new B.C.G. on the dog bladder," Urol Res, 14(4): 207-210.
Pusztai (2007) "Markers predicting clinical benefit in breast cancer from microtubule-targeting agents," Annals of Oncology. 18(12): xii15-20.
Wientjes et al. (1991) "A method to study drug concentration-depth profiles in tissues: mitomycin C in dog bladder wall," Pharm Res, 8(2): 168-173.
Wientjes et al. (1991) "Bladder wall penetration of intravesical mitomycin C in dogs." Cancer Res, 51 (16): 1347-4354.
Wientjes et al. (1993) "Penetration of mitomycin C in human bladder," Cancer Res, 53(14): 3314-3320.

(56) References Cited

OTHER PUBLICATIONS

Wosnitzer et al. (2011) "Predictive value of microtubule associated proteins tau and stathmin in patients with nonmuscle invasive bladder cancer receiving adjuvant intravesical taxane therapy," J Urol, 186(5):2094-100.

Zaske et al. (2001) "Docetaxel :Solid state characterization by X-ray powder diffraction and thermogravimetry," J. Phys. IV France, 11: Pr10-221-pr10-226.

POLYMER-BASED SERUM ALBUMIN SUBSTITUTE

BACKGROUND OF THE INVENTION

Serum albumin is the most abundant plasma protein in animal blood. In humans, human serum albumin (HSA) is present at an average concentration of about 45-50 mg/ml in plasma which corresponds to 52-65% of the total protein content. The molecular weight of HSA is 66,300, it is not glycosylated and has a half-life of about 17 days in the circulation.

Serum albumin acts as a carrier of fatty acid, bilirubin, hormones, drugs and metal ions by reversibly binding these agents. Albumin functions in the delivery of biologically relevant materials and scavenges waste materials for elimination. One of its major functions, associated with its high concentration, is to provide much of the osmotic pressure in blood that is required to balance the high concentration of osmotically active macromolecules in the cytoplasm of blood cells. In addition, a pressure balance must be maintained across the endothelium between the interior of blood vessels and the interstitial space to avoid undue water movement and tissue swelling (edema). HSA provides about 80% of the colloid osmotic pressure that balances the hydrostatic pressure in the vascular tree.

Replacement of serum albumin is particularly important in acute conditions such as burns, severe blood loss, cardiac surgery, shock or other conditions where potentially life threatening fluid shifts occur unless lost volume and osmotic activity are replaced.

One approach for production or improvement of a plasma protein is to produce it by recombinant techniques. This has been done for HSA but because of the large amounts required for clinical purposes worldwide, this approach is cost prohibitive.

For decades, attempts have been made to use various polymers as cost effective serum albumin substitutes. Polysaccharides (modified starch such as hydroxyethyl starch (HES) or dextran) and collagen (i.e., gelatin) derivatives have been used as plasma expanders. Solutions of such macromolecules ("colloids"), rely on molecular size for their ability to produce the desired osmotic gradient between plasma and interstitial space. However, all the synthetic colloids increase plasma viscosity significantly, which is detrimental to the heart and circulatory system and all the synthetic colloids have effects on whole blood rheology, including red cell aggregation. While dextran and FEES are or have been used as substitutes for serum albumin with respect to plasma expansion, they increase plasma viscosity dramatically because of their broad molecular weight distribution and high average molecular weight (Mw about 670,000 for hetastarch). Buffered salt solutions ("crystalloids") are also employed and are more cost effective than colloids, but they must be administered in much larger volumes and their effects are very short term. None of the polysaccharide or collagen based derivatives nor salt solutions perform any function of serum albumin other than its role in the maintenance of osmotic pressure.

Various polymers have also been used or proposed as drug delivery vehicles or as carriers for biologically active compounds. Such polymers have included dendritic polymers, including dendrimers and hyperbranched polymers such as hyperbranched polyglycerol (HPG) (for example see: Sunder, A., et at (1999) Angew Chem. Int. Ed. 38:3552-55; international patent application publication WO 2004/072153; and United States patent application publication 2005/0048650). Linear polyethylene glycols have been used in drug delivery and have also been proposed for use in perfusates and solutions for organ and tissue preservation (e.g. see U.S. Pat. No. 6,321,909; U.S. Pat. No. 6,616,858; U.S. Pat. No. 6,949,335; United States patent application publications 2001/0037956 and 2006/0024657; and international patent application publication WO 2001/01774). In one publication, hyperbranched polymers containing a porphyrin core were proposed as hemoglobin substitutes (see international patent application PCT/GB2004/004841, now published as WO 2005/052023).

SUMMARY OF THE INVENTION

It has now been discovered that hyperbranched polyether polyols including hyperbranched polyglycerol (HPG) are particularly good serum albumin substitutes and may be used as the basis for blood/plasma substitutes having viscosities more closely aligned to that provided by native serum albumin than the colloidal substitutes proposed or used to date. Furthermore, such polymers can be made to mimic other functions of serum albumin such as the capacity to carry fatty acids.

The new use of hyperbranched polymers provided by this invention is distinctly different from previous proposals which suggested using hyperbranched polymers as drug delivery vehicles or carriers. In the present invention, blood and serum may be replaced or expanded through the use of much larger amounts of hyperbranched polymer than would have been previously contemplated in the art for drug delivery. This invention also is distinctly different than the mere use of a hyperbranched polymer as an outer covering for a porphyrin molecule in the production of a hemoglobin replacement.

This invention includes the preparation of derivatized hyperbranched polymers not only for use as serum albumin substitutes but also to provide biologically active moieties. For example, this invention includes the use of hyperbranched polymers suitable as serum albumin substitutes in combination with such polymers modified to carry biologically active moieties including drugs. Various species of such hyperbranched polymers may be combined to provide for both substitution of serum albumin as well as delivery of desired biologically active moieties to target cells and tissues.

This invention also includes novel derivatives of hyperbranched polymers including ones containing hydrophobic (e.g. alkyl) components linked to the hyperbranched polymer through ether linkages which is less likely to be hydrolyzed in vivo. Novel hyperbranched polymers of this invention also include such polymers which combine the presence of such hydrophobic regions and the presence of polyalkylene glycol or polyol substituents which additionally facilitate solubility and longevity.

This invention also provides new methods for preparing hyperbranched polyglycerol (HPG) which methods are particularly suited for the production of high molecular we HPG which advantageously may exhibit narrow ranges of polydispersity. Such high molecular weight HPG molecules were not previously known and will be useful in a variety of applications as suggested in the art with respect to HPG, including biomedical applications (e.g. drug delivery or carrying of biologically active moieties) and in other fields such as catalysts, coatings, adhesives, hydrogels and composites. Such high molecular weight HPG is particularly useful as precursors for preparation of derivatives because of the high level of hydroxyl groups available in each polymer molecule.

DETAILED DESCRIPTION OF THE EMBODIMENTS OF THE INVENTION

The art contains various references describing preparation and uses of hyperbranched polyether polyols including HPG. Various means are known in the art for preparation of derivatives of such polymers, including derivatization with various functional groups and/or the production of copolymers and block copolymers (such as the addition of alkyl groups through ester linkages and the addition of polyalkylene glycol groups). Publications describing preparation of HPG include: U.S. Pat. No. 5,112,876; U.S. Pat. No. 6,469,218; U.S. Pat. No. 6,765,082; U.S. Pat. No. 6,822,068; WO 2000/77070; Sunder, A. et al. (1999) Macromolecules 32:4240-46, (2000) Macromolecules 33:309-14, (2000) Macromolecules 33:1330-37, and (2000) Adv. Mater 12:235-239; Knischaka, R. et al., (2000) Macromolecules 33:315-20; Haag, R., et al. (2000) Macromolecules 33:8158-66, and (2002) J. Comb. Chem, 4:112-19; Kautz, H., et al. (2001) Macromol. Symp. 163:67-73; Karger-Kocsis, J., et al. (2004) Polymer, 45:1185-95; Gao, C. & Yan, D. (2004) Prog. Polym. Sci. 29:183-275; and Tziveleka, L. et al., (2006) Macromol. Biosci. 6:161-169). Sunder, A. et al., (1999) Angew. Chem. Int. Ed. 38:3552-55 contains a description of the preparation of amphiphilic modified HPG.

Hyperbranched polymers for use in this invention may be homopolymers, derivatives of homopolymers, and copolymers including block copolymers. As is discussed in further detail below, derivatives of hyperbranched polymers may include polymers which contain hydrophobic and/or hydrophilic regions which have been added to the polymer. Such regions may be provided by derivatization of terminal or branch hydroxyl groups on the hyperbranched polymer and/or by the addition of polymeric blocks to the branched polymer. An example of substituents which provide hydrophobic regions is the presence of an alkyl group. In this specification, "alkyl" includes any saturated or unsaturated hydrocarbon chain or cyclic moiety which may be substituted by one or more substituents which do not affect the overall hydrophobicity of the alkyl component when added to the branched polymer. For example, methodologies described herein for the addition of alkyl groups to a hyperbranched polymer through an ether linkage employing an epoxide precursor will result in the presence of at least one secondary hydroxyl group within the alkyl component added to the branched polymer.

In order to most closely conform to the mass of serum albumin, polymers for use in this invention may typically have molecular weights in the range of 40,000 to 60,000 g/mol (e.g. about 50,000). However, as shown herein, this molecular weight range is not necessary for serum albumin replacement and indeed, a wider range of molecular weights may be employed advantageously to provide other functions such as carrying of drugs or other biologically active moieties.

This invention contemplates the use of hyperbranched polymers in a wide range of molecular weights and procedures described herein are particularly suitable for production of high molecular weight hyperbranched polymers which may be useful either as an albumin substitute or for a drug carrying agent. Such high molecular weight polymers may have a $M_n$ value in excess of 95,000 g/mol, or at least about 100,000 g/mol, and may be up to about 1,000,000 g/mol or more. Weight average molecular weight may be 1,500,000 or more and may be up to about 5,000,000. Polydispersity of such polymers may be in the range of about 1 to about 3.5 or about 1 to about 3.0, or about 1 to about 2.5, or less than about 2. In some situations, polydispersity may be less than about 1.7.

Various embodiments of this invention make use of hyperbranched polyglycerol (HPG). In some embodiments, the invention employs an HPG composition comprising a core derived from ring-opening polymerization of an excess of glycidol in the presence of an anionic initiator. In some embodiments, the anionic initiator is the singly or multiply-deprotonated form of an alcohol or polyol. The anionic initiator may be the partially-deprotonated form of 1,1,1-tris-hydroxymethylpropane, where there is approximately three alkoxide function per 10 molecule of initiator. The resultant polyanionic polymers may be quenched with proton donor reagent, such as an alcohol or water, to produce a neutral product.

This invention provides the means for the production of high molecular weight HPG previously not obtained in the art which describe polymerization in the absence of a solvent as well as in the presence of solvents such as THF, DMSO, and diglyme. This invention provides a method for the preparation of hyperbranched polyols in which a monomer such as glycidol is added to a hydrogen-active starter compound in the presence of a basic catalyst, in the presence of an emulsifier which is an ether having a boiling point greater than about 90° C. The emulsifier will preferably have a dielectric constant of less than $\in = 7.0$, more preferably less than about 5.0 or less than about 3.0. A suitable emulsifier is dioxane. In some embodiments, the emulsifier is the only non-reactant liquid present during the polymerization reaction.

The polyglycerol branches formed in the polymerization reaction bear a number of secondary and primary alkoxide groups. Further substitution of this core may be effected. For example, polyol (e.g. linear polyglycerol) or polyalkyleneglycol substituents may be bound to up to 80%, about 5% or more, or about 20 to 40%, of the alkoxide groups in the HPG core. The substituents may be derived from a ring opening reaction of a suitable epoxide such as a polyalkyleneglycol epoxide with the alkoxide groups. Such a polyalkyleneglycol substituent may be a polyethyleneglycol (PEG) or variants thereof such as polyethyleneglycol methylether (MPEG).

As a serum albumin substitute, it may be preferable to limit the molecular weight of a polyol or polyalkyleneglycol substituent to between about 100 to about 1,500 daltons, or about 100 to about 1,000 daltons, or about 100 to about 600 daltons. In some embodiments, the molecular weight may be over about 200 daltons. In some embodiments, a particularly useful molecular weight is 350 daltons which for MPEG, represents light ethoxy monomers. However, for other applications such as drug delivery, higher molecular weights of polyalkyleneglycol substituents may be employed (e.g. up to about 20,000 daltons). In some embodiments, a mixture of polymers may be employed. For example, a majority of the polymers present in a composition may fall within lower molecular ranges for PEG components to facilitate serum replacement whereas a limited proportion of the polymers present may comprise higher molecular weight components to facilitate drug delivery.

A further functional derivative may be bound to up to about 50%, or over 1%, or about 5 to about 10%, of the total number of available alkoxide groups. The further functional derivative may be derived from (for example) an alkyl epoxide, a polyalkyleneglycol-alkyl epoxide, or a glycidol aryl ether. Such epoxides may bear alkyl chains of between about 5 and about 30 carbon atoms, or between about 10 and about 30 carbons atoms, or about 15 to about 20 carbon atoms, or over 17 carbon atoms such as 18 carbons atoms. An example of an alkyl epoxide is octadecyl epoxide. The alkyl group is joined to the HPG through an ether linkage, unlike the ester linkages known in the art. Such derivatization creates regions of hydrophobicity surrounded by polar functions, conditions now shown herein to mimic the fatty acid binding sites in HSA. Procedures for preparation of such derivatives may also be adapted from the art, for example from the preparation of $C_8$ and $C_{16}$ ester modified HPG (Sunder et al. (1999) Angew. Chem. Int. Ed. 38:3552) or for the modification of other dendritic polymers (e.g. Walliman, P., et al. (1996) Helvetica Chima Acta. 79:779-88).

A further functional derivative may be the presence of anionic groups, which can bind metal ions such as calcium ions. Some of the HPG hydroxyl groups, for example up to about 50%, can be converted to carboxylic, phosphonic or sulphonic acid groups by suitable chemical modification. For example, this group may be phosphonic acid. The anionic nature of the resulting polymer increases the circulation half life to the polymer while in plasma.

Further functional derivatives may include the presence of amino or amine groups. Furthermore, this approach may be adapted to the preparation of specific derivatives which carry specific biologically active moieties such as peptides. Alkoxide groups may be converted to $NH_2$ groups or groups containing an $NH_2$ functionality. For example, $NH_2$ functionalities can be converted to iodoacetamide equivalents and coupled with a cysteine terminated peptide, thereby mimicking the adhesive prothrombotic function of platelets. Specific peptides may also be coupled to aldehyde groups generated by oxidation of the 1,2 diol groups in HPG. Modification with amino groups alone will provide a cationic polymer useful for nucleic acid delivery (see WO 2004/072155) or for scavenging undesirable proteins such as prions (see Supattapone, S., et al. (1999) P. NAS 96:14529-34). Also, the addition of branched amino groups would facilitate conjugation of chelating agents, for example MRI contrast agents (see Wiener, E., et al. (1994) Magn. Research Med. 31:1-7 and Kobayashi, H., et al. (2003) Bioconjugate Chem. 14:388-41). As shown in the examples below, the presence of amine functionalities permits bilirubin scavenging.

A further example of a derivative which contains a biologically active moiety is the addition of folic acid. Folic acid receptors are more abundant in cancer cells, providing for specific delivery of drugs to tumors using polymers of this invention (see Kano, K., et al, (1999) Bioconjugate Chem. 10:1115-21 and Quintana, A., et al. (2002) Pharmaceutical Research 19:1310-16).

A further example of a derivative that includes a biologically active moiety is the presence of 5-aminolevulininic acid, which is a carrier for the delivery of ALA to cells for applications in photodynamic treatment. Irradiation with light and subsequent reaction with oxygen creates tissue damaging singlet $O_2$ (see Battah, S., et al. (2001) Bioconjugate Chem. 12:980-88).

Other biologically active moieties could be joined to HPG or associated with HPG for use in this invention. Further examples include sialic acid having potential for inhibition of viral infections (Landers et al. (2002) J. Infect. Dis. 186:1222-30) or the additional of naphthyl or sulphonate groups which may have antiviral activity (e.g. Witvrouw, M., et al. (2000) J. Med. Chem. 43:778-83). Other descriptions of design of specialized glycodendrimers are found in the art (e.g. Turnbull, W. B. (2002) Reviews in Molecular Biotechnology 90:231-55) describing carbohydrate coated branched polymers useful as glycocarriers.

Hyperbranched polymers for use in this invention may also be associated with selected drugs, including hydrophobic drugs as is disclosed in the art. A proportion of polymer moieties for use as a serum albumin substitute for this invention may be associated with such drugs or a small proportion of the polymers present in a serum or blood replacement composition may be utilized for such purposes.

The branched materials employed in this invention can be synthesized to have narrow molecular weight distribution. The hyperbranched nature of the core molecule makes it very compact in solution, unlike a linear polymer or modified polysaccharide such as hydroxyethyl starch. It also provides these structures with low intrinsic viscosities, while the multiple reactive end groups provide many sites for derivatization with (for example) hydrophobic binding sites and addition of poly(ethylene glycol) (PEG) end chains to protect the molecule from host defense systems thereby improving the circulation time in the blood stream.

The high molecular weight HPG of this invention itself can be used as an albumin substitute after appropriate derivatization with hydrophobic groups, acid groups and amine groups. For example, glycidol and alkene epoxide can be copolymerized to get a hydrophobically modified high molecular weight polyglycerol.

Embodiments of this invention include a sterile blood/plasma expander or blood/plasma substitute or replacement composition comprising one or more species of the hyperbranched polymer described above in a concentration of (for example) 0.5-5% (w/v) in aqueous solution. Liquid concentrates which may be diluted for use are also included. The solution may further comprise cations or salts providing such cations including at least one of $Na^+$, $Ca^{2+}$, $Mg^{2+}$ or $K^+$ at physiologically acceptable concentration or to be diluted to such amounts. The solution may further comprise one or more suitable buffers such as, but not limited to, lactate or bicarbonate, in an amount which will maintain the pH of the resulting composition at physiological pH (for example at a pH of 7.2-7.8). Other known physiologically acceptable diluents and excipients may be present. The resultant solution may have an intrinsic viscosity of less than 10 mL/g. Also included are dry, sterile preparations of such compositions.

Embodiments of this invention include a dry, sterile composition comprising a dry sample of one or more species of the hyperbranched polymer as described above. The dry compositions may further comprise at least one salt of the formula $M_aX_b$, where X=chloride or halide or other mono-, di-, or trianionic species, and $M=Na^+$, $Ca^{2+}$, $Mg^{2+}$ or $K^+$. The magnitude of a and b are dictated by the ionization state of M and X, providing a neutral salt $M_aX_b$ which is overall neutral in charge (e.g. NaCl). The dry composition may further comprise one or more suitable buffers such as, but not limited to, Q(lactate) or Q(bicarbonate) where Q is an appropriate counterion (for example, $Na^+$, $Ca^{2+}$, $Mg^{2+}$ or $K^+$). Other physiologically acceptable excipients may be present. The components of the dry composition may be present in a suitable ratio which, when hydrated with a suitable volume of sterile diluent such as water, affords a sterile plasma expander or blood/plasma substitute composition as described above. The intrinsic viscosity of the resulting composition may be less than about 20 mL/g. In some embodiments, it may be less than about 10 mL/g.

A synthetic strategy to make HPG involves the synthesis of hyperbranched polyglycerols by anionic ring opening multibranching polymerization of glycidol using a partially deprotonated polyalcohol as an initiator. In some embodiments the polyalcohol is trimethylolpropane (TMP). The hydroxyl-hydrocarbon may be partially deprotonated using potassium methylate (Scheme I). Limited deprotonation of TMP (only 10% of the total OH groups are deprotonated) and slow monomer addition help to control molecular weights in order to provide narrow polydispersity. The polymerization proceeds with each alkoxide group reacting with the epoxide ring on its unsubstituted end, generating a secondary alkoxide and a primary alcohol group. Rapid cation-exchange equilibrium between primary and secondary hydroxyl groups leads to chain propagation from all the hydroxyl groups in the polymer molecule, producing a hyperbranched structure. The hyperbranched structure will have numerous hydroxyl end groups (given by the degree of polymerization (DP; one per reacted monomer)+the number of OH groups in the initiator) which are all reactive.

Scheme I. Synthesis of hyperbranched polyglycerol

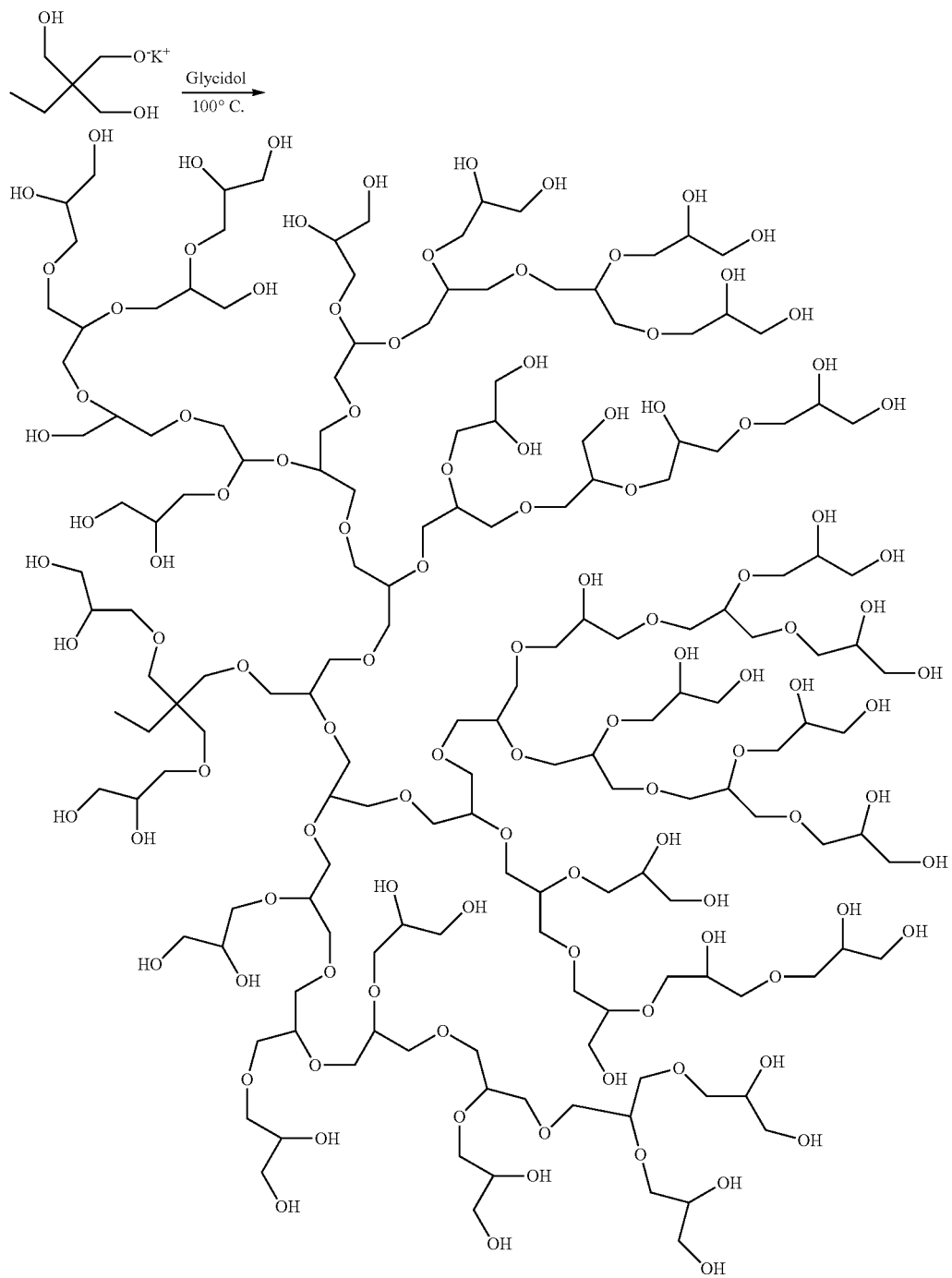

An undesirable side reaction leads to macrocyclic species which can be formed by the initiation of polymerization from a deprotonated glycidol molecule followed by propagation and intramolecular reaction of one of the hydroxyl end groups with the epoxide group. This can be suppressed by slow monomer addition.

For derivatization, a fraction of terminal OH groups may be reacted with, for example, alkyl epoxides bearing appropriate alkyl chains (e.g., C18), creating regions of hydrophobicity surrounded by polar functions, conditions that mimic the fatty acid binding sites in HSA. Further derivatization may utilize similar chemistry whereby PEG epoxides such as poly(ethyleneglycol-methylether) (MPEG) epoxides are reacted with a fraction of the remaining OH functions to provide PEG or MPEG caps (see Scheme II below). Derivatization could also involve the use of alkyl expoxides bearing PEG caps which will place the alkyl chain between the cap and the HPG moiety.

This invention includes the use of a polymer comprising a hyperbranched polyether polyol such as HPG as a substitute for serum albumin in the treatment of a human or non-human animal or for the preservation of a living tissue or an organ. The use may be in the treatment of the animal to expand blood volume in the animal. Also contemplated is the use of such a polymer as a substitute for serum albumin in the preparation of a blood or plasma extender, replacement or substitute. Such polymers may not contain a porphyrin core. This invention also contemplates the use of hyperbranched polymers as described herein as a carrier for a drug or other biologically active moiety and for the preparation of therapeutic medicaments for delivery of such drugs or moieties to target tissues or cells. In particular, high molecular weight hyperbranched polymers of this invention may be employed for delivery of drugs and other biologically active moieties.

This invention also includes a method of expanding blood or plasma volume in a patient in need thereof comprising intravenous administration of an effective amount of a polymer or composition as described herein. A patient in need of such treatment may include patients suffering from blood loss, hemorrhage, burns, shock or who are undergoing surgery. It is within the skill of the medical practitioner to make use of compositions described herein for intravenous administration and to determine appropriate quantities, delivery rates, concentrations of components and relative presence of different species of polymers in accordance with this invention in order to provide an appropriate balance with respect to serum substitution and/or delivery of drugs or biologically active moieties. For example, the proportion of polymer molecules in a particular composition for administration to a patient which carry a drug or other biologically active moiety intended to be delivered to a cell or tissue, as compared to polymer molecules in the composition which act as a serum albumin replacement may be about 1:20, or about 1:50, or about 1:100, or about 1:1,000, or about 1:10,000 or about 1:100,000 or less.

This invention also includes the use of polymers and compositions of this invention for maintaining a tissue or organ in a patient in need thereof. Also included is a method of maintaining a tissue or organ in a patient in need thereof, the method comprising perfusion of the tissue or organ with an effective amount of a solution containing a polymer or composition of this invention. Patients in need thereof include patients undergoing surgery or organ or tissue transplants. Such solutions may be oxygenated by known means.

This invention also includes any intravenous delivery apparatus or storage container for intravenous fluids containing a polymer or composition of this invention. Examples include sterile bags for storage and intravenous delivery, syringes, pump driven delivery apparatus and the like.

In another aspect, this invention includes the use, in a subject in need thereof, of the above-described compositions as a plasma expander, serum albumin substitute, or blood-free blood substitute or for the preparation of such medicaments.

In yet other aspects, the invention includes the use of the above-described compositions as small molecule drug, biologically active moiety, polypeptide, or polynucleotide delivery agents, or MRI contrast agents, or as scavenging agents or for the preparation of such medicaments.

The information above and examples described below are presented within this application in order to more fully describe the invention, they should not be considered limiting with respect to the spirit or scope of the invention described herein.

EXAMPLES

Synthesis

HPG polymers with degree of polymerization (DP) of 30 were made according to the methods of Sunder, A., et al. (1999) Macromolecules 32:4240) in order to standardize conditions and to check reproducibility. The polymers were characterized by NMR and GPC and results are shown in Table 1.

All chemicals were purchased from Sigma-Aldrich Canada Ltd. (Oakville, ON) and used without further purification except the following. Glycidol (96%) was purified by vacuum distillation and stored over molecular sieves in a refrigerator (2-4° C.). Anhydrous diglyme and dioxane were obtained from Aldrich and used without further drying. Molecular weights and polydispersities of polyglycerol samples were determined by gel permeation chromatography (GPC) on a Waters 2690™ separation module fitted with a DAWN EOS™ multiangle laser light scattering (MALLS) detector from Wyatt Technology Corp. with 18 detectors placed at different angles (laser wavelength=690 nm) and a refractive index detector (Optilab DSP™ from Wyatt Technology Corp.). An Ultrahydrogel™ linear column with bead size 6-13 µm (elution range $10^3$-$5\times10^6$ Da) and an Ultrahydrogel™ 120 with bead size 6 µm (elution range 150-$5\times10^3$ Da) from Waters were used. An aqueous 0.1 N $NaNO_3$ solution was used as the mobile phase at a flow rate of 0.8 mL/min. The dn/dc value for polyglycerol was determined to be 0.12 g/ml in aqueous 0.1 N $NaNO_3$ solutions and was used for molecular weight calculations. The data were processed using Astra software provided by Wyatt Technology Corp.

Intrinsic viscosity, hydrodynamic radii, Mark-Houwink parameters and radius of gyration ($R_g$) were obtained from a triple detector from Viscotek Corp. connected to the GPC system, which utilizes refractive index, 90-degree light scattering and intrinsic viscosity determinations. The data were processed using the software provided by Viscotek. Hydrodynamic radii ($R_h$) were also obtained from a quasi elastic light scattering (QELS) detector (Wyatt Technology Corp.) which was connected to the MALLS detector using the Astra software.

After polymerization, the polymers were dissolved in methanol, neutralized by passing three times through a column containing cation exchange resin (Amberlite IRC-150). Polymers were then precipitated into excess of acetone and stirred for 1 hour. Acetone was decanted out and this procedure was repeated once more. Dialysis of polymers was done for three days against water using cellulose acetate dialysis tubing (MWCO 1000 or 10000 g/mol) with the water being changed three times per day. The polymers were generally non-sticky, highly viscous materials that did not flow. Dry polymer was obtained by freeze drying.

Narrow molecular weight distributions were obtained for lower molecular weights, as reported in the literature. Higher molecular weight polymers were synthesized by employing higher monomer/initiator core ratios but the products have polydispersities. This was the case even when a lower monomer addition rate was employed. This is consistent with the findings of earlier researchers who reasoned that this is due to an increase in viscosity of the polymerization mixture in the later stages of the reaction (reactions are carried out without solvent, in neat liquid monomer), which slows down the reversible cation exchange. By increasing stirrer speed and using diglyme (diethylene glycol dimethyl ether) as an emulsifying solvent (diglyme is a nonsolvent for polyglycerol) in order to dilute the monomer and reduce viscosity of the polymerization mixture they reported obtaining unimodal, narrowed molecular distributions. However, when diglyme was used herein, polymers tended to higher molecular weights (e.g. above 100,000) with polydispersities around 2.

The $^1$H NMR of the polymers showed the presence of TMP initiator. Peaks at 0.8 (3H) and 1.3 ppm (2H) are due to the methyl and methylene groups of TMP. The protons of polyglycerol appear as a broad resonance between 3.3 and 3.9 ppm. The hydroxyl protons appear at 4.7 ppm in methanol-d6.

$^{13}$C NMR gives information on both the degree of polymerization (DP) and degree of branching (DB). The assignment of peaks is well described in the literature. As shown in Table 1 the DB values ranged between 0.56 and 0.63, meaning that this fraction of monomers exhibit branch points. Higher molecular weight samples showed higher degrees of branching. The distribution of structural units was similar to reported values. The molecular weights obtained from NMR were higher than implied by the monomer/initiator ratios employed. However, it is to be noted that this method is not convenient for high molecular weight polyglycerols (>10,000 g/mol) as the difference between the integrations of terminal and dendritic units becomes too low to allow accurate molecular weight estimates.

Molecular weight and polydispersity of the polymers were obtained by GPC analysis using both a Viscotek triple detector, which utilizes refractive index, 90-degree light scattering and intrinsic viscosity (IV) determination and a multi-angle laser light scattering detector (MALLS) that provides a measure of molecular weight distribution that does not rely on structural assumptions. However, MALLS were not particularly accurate for the low molecular weight samples.

The intrinsic viscosity (IV) values were low as anticipated for hyperbranched polymers and did not vary much with molecular weight. By contrast the IV value for serum albumin was about 3-5 whereas the following Values were exhibited for previous albumin substitutes: heta starch (16.25), PVP (14.17), dextran 58 (20.2) and dextran 94 (26.78).

A decrease in IV implies a more compact structure per gram, as it is a direct measure of the increment in viscosity per grain of added material. Presumably this means that as the structures get larger and the radius of gyration, Rg, increases, the chains are less constrained by their neighbors and can occupy a higher local density away from the core. Near the core excluded volume effects would tend to force the chains into more extended configurations. The compactness is also reflected in the Rg values themselves as these were found to be less than 10 nm even for a polymer with Mn of 300,000 g/mol. For comparison, Rg for a typical linear polymer of molecular weight 30,000 would be about 7 nm while Table 1 shows that this value of Rg is associated with a lowerbranched polymer of $M_n$ 112,000.

GPC chromatograms of some polymers, especially those with higher molecular weights, showed the presence of a low molecular weight tail, which is expected to be predominantly the macrocyclics. To remove this low molecular weight fraction the polymer RKK-7 was subjected to dialysis. Two membranes with 1,000 and 10,000 mol. wt cut offs were used. It was found that polymer dialysed with 10,000 mol wt cut off was devoid of the low molecular weight tail and the polydispersity narrowed down to 1.9. The polymers with different molecular weights purified by dialysis were utilized in initial animal testing.

Dioxane was also employed as an emulsifying agent otherwise following the procedure described above. The initiator as well as the polymer is insoluble in dioxane. Surprisingly, very narrowly dispersed high molecular weight polymers were obtained without the need for dialysis. The polymers were obtained by precipitation of methanolic solution in acetone. The polydispersities were below 1.5 with monomodal distributions (Table 1A). Dialyzation (MWCO 1,000) did not change the molecular weight characteristics.

TABLE 1

Polyglycidol synthesis and characterization

| Polymer Code | Glycidol/TMP | TMP/MeOK | Yield % | DB | DP | Rh (QELS) (nm) | Triple Detector $M_n$ | PD | IV (mL/g) | Rg (nm) | Multi-angle Light Scattering $M_n$ | PD | Rg (nm) |
|---|---|---|---|---|---|---|---|---|---|---|---|---|---|
| RKK-1 | 30 | 10 | 89 | 57 | 40 | 1.9 | 4250 | 1.3 | 5.7 | 2.2 | — | — | — |
| RKK-2 | 30 | 10 | 86 | 58 | 37 |  | 4800 | 1.2 | 5.6 | 2.2 | — | — | — |
| RKK-5 | 30 | 30 | 80 | 56 | 40 |  | 4600 | 1.3 | 6.1 | 2.3 | — | — | — |
| RKK-6 | 270 | 30 | 71 | 63 | 355 | 5.1 | 14500 | 3.2 | 5.1 | 4.1 | 17800 | 2.4 | — |
| RKK-7 | 540 | 30 | 63 | 62 | — | 5.4 | 15400 | 6.3 | 5.2 | 5.1 | 36200 | 2.6 | 5.0 |
| RKK-8 | 325 | 30 | 79 | — | — |  | 12500 | 5.3 | 5.0 | 4.6 | 25600 | 2.5 |  |
| RKK-11 | 270 | 30 | 84 | — | — | 13.7 | 112000 | 3.9 | 3.9 | 7.5 | 140000 | 2.9 | 7.9 |
| RKK-12 | 270 | 30 | 79 | — | — | 16.7 | 305000 | 2.7 | 3.7 | 9.5 | 318000 | 2.2 | 8.0 |

(Experimental: Glycerol = 25 mL, time = 17 hours, temp = 95° C.; DB (degree of branching) and DP (degree of polymerization) are calculated from $^{13}$C NMR, monomer addition rate was 0.9 mL/min for RKK-8, 25 mL diglyme was used in the preparation of RKK-11 and 12)

TABLE 1A

Characteristics and solution properties of high molecular weight hyperbranched polyglycerols (homopolymers)

| Polymer Code | Solvent | Theor. $M_n \times 10^{-3}$ | Yield % | $M_n \times 10^{-3}$ | $M_w \times 10^{-3}$ | $M_w/M_n$ (PD) | IV (mL/g) | $R_h$ (QELS) (nm) | $R_g$ (nm) (TDA) | $R_h$ (nm) (TDA) | α |
|---|---|---|---|---|---|---|---|---|---|---|---|
| RKK-1 | none | 2.3 | 89 | 4.2 | 5.5 | 1.3 | 3.3 | 1.9 | 2.2 | 1.7 | nd |
| RKK-2 | none | 2.3 | 80 | 4.8 | 5.7 | 1.2 | 3.4 | nd | 2.2 | 1.7 | nd |
| RKK-3 | none | 2.3 | 86 | 4.6 | 6.0 | 1.2 | 3.2 | nd | 2.3 | 1.8 | 0.43 |
| RKK-6 | none | 20 | 71 | 25 | 40 | 1.6 | 3.9 | 3.0 | 3.5 | 2.7 | 0.35 |
| RKK-7 | none | 40 | 63 | 42.5 | 76.5 | 1.8 | 3.9 | 3.6 | 4.3 | 3.3 | 0.34 |
| RKK-342 | Diglyme | 20 | 81 | 106 | 217 | 2.0 | 3.6 | 3.9 | 6.2 | 4.8 | 0.27 |
| RKK-11 | Diglyme | 40 | 76 | 106 | 307 | 2.9 | 3.8 | 4.8 | 6.8 | 5.2 | 0.35 |
| RKK-12 | Diglyme | 40 | 68 | 266 | 771 | 2.9 | 3.8 | 6.6 | 9.3 | 7.2 | 0.37 |
| RKK-341 | Diglyme | 60 | 70 | 871 | 1475 | 1.7 | 3.8 | 7.8 | 12.5 | 9.6 | 0.39 |
| RKK-27 | Dioxane | 20 | 83 | 359 | 491 | 1.4 | 3.3 | 6.3 | 9.2 | 7.0 | 0.31 |
| RKK-337 | Dioxane | 40 | 90 | 540 | 589 | 1.1 | 3.0 | 6.8 | 9.2 | 7.1 | 0.34 |
| RKK-340 | Dioxane | 60 | 79 | 670 | 728 | 1.1 | 3.1 | 6.6 | 9.2 | 7.1 | 0.31 |

α is the conformation coefficient determined from the slope of log Rg-log M plot;
$R_h$ hydrodynamic radius;
$R_g$ radius of gyration The choice of emulsifying agent permits the production of very high molecular weight HPG with narrow and/or low polydispersities. Limited deprotonation of TMP (only 10% of the total OH groups are deprotonated) and slow monomer addition are important for controlling molecular weight with narrow polydispersity. The polymerization proceeds with each alkoxide group reacting with the epoxide ring on its unsubstituted end, generating a secondary alkoxide and a primary alcohol group. Rapid cation exchange equilibrium between primary and secondary hydroxyl groups leads to chain propagation from all hydroxyl groups in the polymer chain, leading to a hyperbranched structure. An undesirable side reaction leads to macrocyclics which can be formed by the initiation of polymerization from a deprotonated glycidol monomer followed by propagation and intramolecular reaction of one of the alkoxide end groups with the epoxide group of the glycidol initiator. This is suppressed by slow monomer addition and by a faster propagation reaction. So, under identical polymerization conditions, the route to narrow polydispersity lies in the rapid cation exchange process. It is possible that since dioxane is a less polar solvent (dielectric constant, $\in$=2.2) than diglyme ($\in$=7.0) the exchange process is more favored, leading to more branched (discussed later) and narrowly dispersed polymers.

These high molecular weight HPGs are very useful materials for applications utilizing further chemical manipulation owing to the presence of the very large number of hydroxyl groups. For example, HPG-10 which has a $M_n$ of 670,000 has about 9,000 OH groups or more. It is to be noted that this corresponds to a generation 11 PAMAM dendrimer. However, unlike the synthesis of a generation 11 dendrimer in 10 multisteps with same number of purification steps, these polymers were synthesized in a single step.

Derivatization

The initial target MW for a derivatized HPG was about 50,000 g/mol. A single pot synthesis based on the epoxide ring opening reaction (described below) was employed. This synthetic methodology avoids the formation of ester linkages, which may be susceptible to enzymatic hydrolysis by esterases. Numerous derivatives of the type desired may be prepared and a selection of these is presented in Table 2.

A three neck round bottom flask was used for the polymerization reactions. One neck was connected to an argon inlet and another closed with a stopper. The third neck was closed with a rubber septum and was used for monomer addition. Initially, the flask was flushed with argon and a weighed amount of trimethyloyl propane (120 mg) was added to it. Required volume of potassium methylate (100 µL) solution in methanol was then added to it and the mixture was stirred for 15 minutes. The flask was kept in an oil bath at 95° C. and the excess methanol was evaporated in vacuum with stirring. After this the mechanical stirrer was connected to replace the stopper. Glycidol (5 mL) was syringed out and added drop wise to the reaction flask using a syringe pump. As the reaction progressed the mixture became viscous, however, the mechanical stirrer was able to mix it efficiently. After complete addition, the reaction mixture was stirred for additional 5 hours. Then a calculated amount of octadecyl epoxide (1 g) was added and continued the stirring at 95° C. for 24 hours. PEG-epoxide (15 mL) was then added slowly using the syringe pump in 12 hours time. The whole mixture was then stirred for additional 5 hours. Methanol was then added to the mixture to dissolve the polymer followed by neutralizing passage through a cation exchange resin (Amberlite™ IRC-150). Unreacted octadecyl epoxide was extracted with hexane. The methanol was removed in vacuum to get the polymer which was dialyzed against water using a dialysis membrane (1000 MW CO). Dry polymer was obtained after freeze drying.

In particular cases, a HPG of Mn about 7000-8000 g/mol was first synthesized. Long chain alkyl or phenyl groups were coupled to 5-10% of the approximately 100 end groups present by ring opening reaction of an alkene epoxide or glycidyl phenyl ether; phenyl alkyl groups may also be used to increase local hydrophobicity. Finally, MPEG caps were added to 20-40% of the —OH groups (whose number does not change since one is generated by each ring opening) by continuing the epoxide reaction using epoxide terminated MPEG with Mn being about 400-600 g/mol. MPEG epoxide was added dropwise in order to get a uniform distribution among the OH groups; the reaction is quantitative. The final product was washed with hexane to remove unreacted alkyl epoxide.

In a particular case exemplified in Scheme II (below), hyperbranched polyglycidol was prepared by anionic ring opening multibranching polymerization of glycidol from partially deprotonated trimethylolpropane using potassium methylate. The target molecular weight for the HPG was 7000-8000 g/mol. In the second step about 2.5% terminal OH groups (total number of OH groups=degree of polymerization+OH groups in the initiator) are reacted with octadecene oxide to create regions of hydrophobicity. In the third step poly(ethyleneglycol-monomethylether) epoxide is reacted with about 40% of remaining OH groups. The monomers, glycidol and MPEG-350 epoxide are added slowly to produce a uniform distribution leading to narrow polydispersity. The single pot synthesis is carried out by sequential addition of monomers with final removal of unreacted alkyl epoxides by washing with hexane and dialysis.

All polymers were subjected to dialysis and then characterized by $^1$H NMR and GPC. NMR showed the presence of alkyl groups, a peak corresponding to the OMe of MPEG-epoxide and the absence of any epoxide groups. Even though quantitative conversions were obtained for MPEG-epoxide, about 50% conversion was achieved for octadecene epoxide (ODE). As an example, compound RKK-43 had 2.5% octadecyl groups and 21% MPEG chains with respect

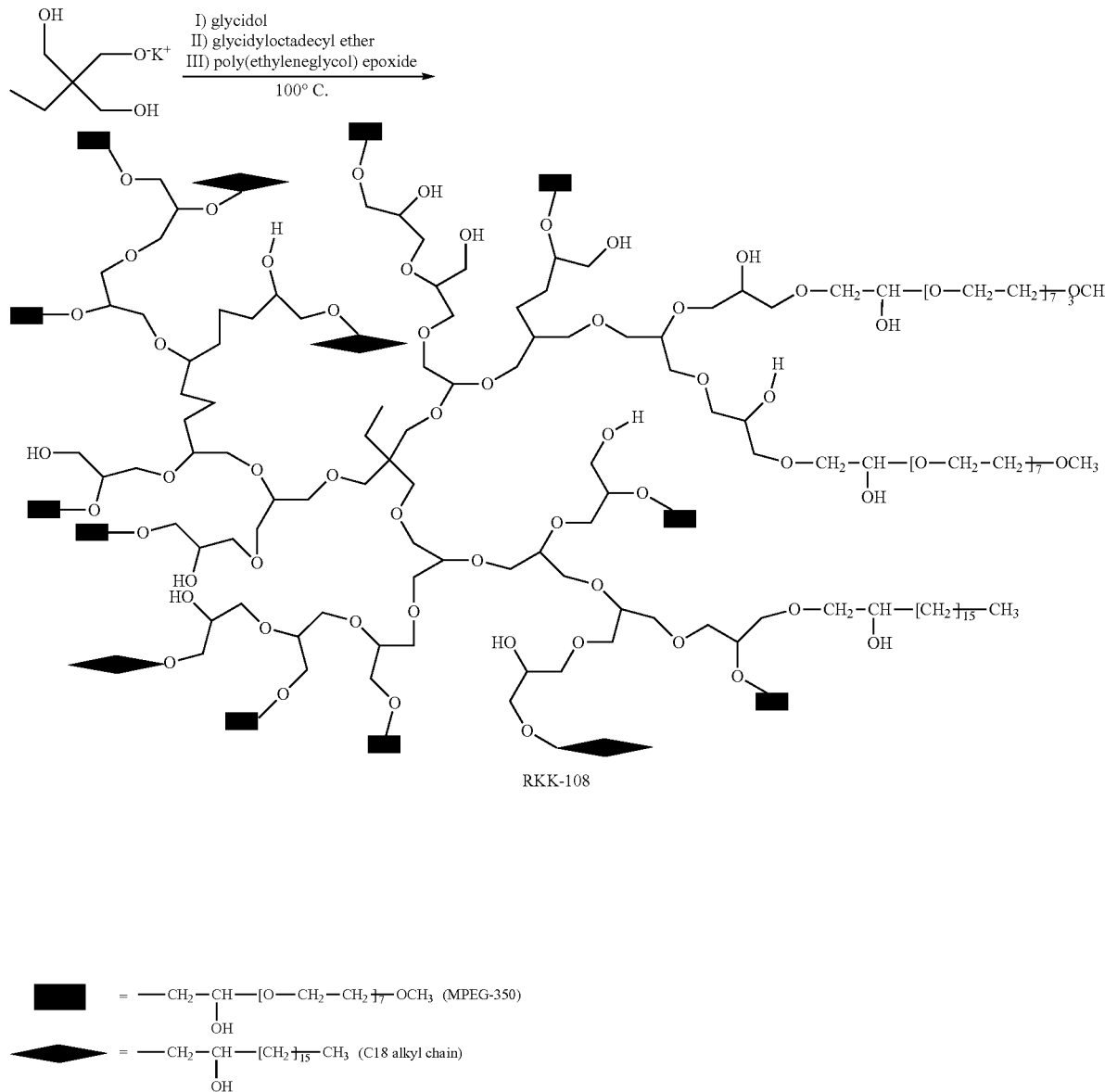

Since PEG chains increase the IV, a balance was sought between the number of MPEG chains and their MW. However, since it is ideal for the polymer to be retained in the circulation for a suitable length of time, the desired balance may in practice be determined empirically. The alkene epoxide was synthesized by reaction of long chain alkenes such as octadecene and m-chloroperbenzoic acid and the epoxide terminated MPEG by reaction of MPEG, sodium hydroxide and epichlorohydrin.

to the total OH groups (approx. 100 per molecule) as measured by $^1$H NMR, taken in DMSO-d6 to allow quantitative integration of all OH groups. The Mn of the final polymer was 44,000, PDI of 2.5 and IV=7.2 mL/g (compared to IV about 6 ml/g for the same HPG core). Results for a range of other products are summarized in Table 2. The IV values are slightly higher than that of HSA, which is 3.7 mug. However, it is to be noted that Dextran 70, a clinically utilized plasma expander, has an IV of about 26 ml/g.

TABLE 2

The physical characteristics of the copolymers

| Polymer Code | Co-monomer (R) | R[a] % | PEG[a] % | No of R gps in a polymer chain[b] | Triple Detector | | | | MALLS | | | QELS[c] |
|---|---|---|---|---|---|---|---|---|---|---|---|---|
| | | | | | $M_n \times 10^{-4}$ | PD | IV (mL/g) | Rg (nm) | $M_n \times 10^{-4}$ | PD | Rg (nm) | Rh (nm) (1 mg/ml) |
| RKK-43 | ODE | 2.5 | 20.7 | 6.8 | 3.89 | 2.23 | 7.17 | 5.71 | 4.40 | 2.50 | — | 40 |
| RKK-55 | ODE | 1.7 | 25.5 | 4.8 | 2.87 | 2.67 | 7.90 | 5.70 | 5.10 | 1.78 | — | |
| RKK-56 | ODE | 1.8 | 40 | 3.8 | 3.66 | 2.50 | 7.90 | 6.06 | 5.10 | 2.15 | — | |
| RKK-71 | ODE | 1.6 | 27 | 3.9 | 3.61 | 1.94 | 8.01 | 5.60 | 4.66 | 2.10 | | |
| RKK-108 | ODE | 2.6 | 37.5 | 9.5 | 6.65 | 1.77 | 7.94 | 6.66 | 8.50 | 1.50 | 13 | 20 |
| RKK-110 | ODE | 0.8 | 18.3 | 4.6 | 6.76 | 2.77 | 8.12 | 7.69 | 8.70 | 3.74 | 28 | |
| RKK-153 | ODE | 4.6 | 40 | 15 | 7.80 | 3.1 | 8.2 | 25.4 | 12.00 | 3.2 | 9.7 | 15 |
| RKK-148 | ODE | 4.5 | 71 | nd | 13.8 | 10.5 | 9.72 | 14.4 | 16.00 | 8.0 | 22.8 | 28 |
| RKK-99 | — | — | 37 | — | 2.50 | 5.55 | 8.18 | 6.60 | 3.90 | 5.30 | — | 10 |
| RKK-52[d] | ODE | 5.9 | 32 | nd | 45.00 | 6.30 | 12.50 | 22.75 | 119.00 | 3.00 | 70 | |
| RKK-112[e] | ODE | 3.1 | 28 | nd | 39.00 | 8.67 | 13.08 | 24.29 | 74.70 | 4.72 | 58 | |
| RKK-111[f] | Brij 76 | 2.9 | 50 | nd | 91.40 | 2.77 | 8.36 | 8.36 | 101.00 | 2.39 | 8.2 | 16 |
| RKK-122 | GHDE | 3 | 34 | nd | 19.00 | 1.70 | 8.50 | 9.60 | 25.00 | 2.00 | 37 | |
| RKK-117 | PGE | 10 | 30 | nd | 7.60 | 4.5 | 8.50 | 9.10 | 11.30 | 3.20 | 12.7 | 10 |
| RKK-139 | GNPE | 2 | 28 | 4.1 | 3.0 | 3.3 | 8.4 | 6.2 | 4.0 | 2.6 | | 7 |
| RKK-120 | GNPE | 5.8 | 21 | 33 | 6.7 | 3 | 7.4 | 7.5 | 10.0 | 2.7 | | 8 |
| RKK-140 | GNPE | 10.5 | 38 | 70 | 10.6 | 3.1 | 6.9 | 8.7 | 17.0 | 2 | 9.6 | 8 |
| RKK-141 | GNPE | 15 | 26 | 542 | 33.3 | 18.4 | 5.2 | 14.7 | 80.0 | 5.7 | 33 | HI |

[a]These values are with respect to Glycidol (OH groups)
[b]Calculated from the number average molecular weight (MALLS) and composition
[c]Measured using a microcuvette
[d]20% hydroxylation of TMP,
[e]PEG-550 was used,
[f]epoxide of Brij-76 was used,
nd) not determined due to suspected intermolecular association The amount of octadecyl chains incorporated was increased by increasing the extent of deprotonation of TMP hydroxyl groups (20%-30% instead of 10%). Some of these polymers were found to show ultra high molecular weights and broad polydispersity, indicating the formation of intermolecular aggregates.

Since conversion of the octadecene epoxide was not quantitative with 10% deprotonation of TMP hydroxyl groups, a more reactive epoxide was sought in order to avoid a purification step to remove unreacted monomer. To this end, the epoxide of Brij 76 (decaethylene glycol octadecyl ether) was used as a comonomer. It was found to be very reactive and up to 13% incorporation could be achieved. The aqueous solutions of these copolymers were however turbid, perhaps due to the presence of large amounts of octadecyl groups, leading to phase separation. These copolymers were later found to be insoluble after 3 months of storage in the freezer.

Like octadecene epoxide, conversions up to only 50% were obtained for glycidyl hexadecyl ether (GHDE) suggesting that phase separation of the reaction mixture is the reason for low reactivity. Quantitative conversions were obtained for phenyl glycidyl ether (PGE) and glycidyl 4-nonyl phenyl ether (GNPE) which were miscible with glycidol and were added as their mixtures.

Higher incorporation can be achieved by increasing the amount of alkoxide groups in the core by adding deprotonating agents such as diphenyl methyl potassium to the HPG. Higher alkyl content can also be achieved by using glycidyl alkyl ethers having shorter alkyl chains (e.g. $C_{10}$). Up to 15% alkyl incorporation was obtained by a combination of these two approaches.

In order to determine whether the polymers formed intermolecular associations, the hydrodynamic radii (Rh) were measured using quasi-elastic light scattering (QELS). Polymer samples of known concentrations were made and subjected to QELS analysis in a microcuvette. The average Rh values of various polymers at 1 mg/ml solutions are shown in Table 1 above. RKK-99, which does not contain alkyl groups has an average hydrodynamic radius of 10 nm. RKK-43, 108 and 153 had different hydrodynamic radii depending on the sample concentration. For example RKK-43 has Rh of 40 nm and 70 nm at concentrations 1 mg/ml and 5 mg/ml respectively indicating possible aggregation. The corresponding Rh values for RKK-108 were 20 and 35 nm. The decreased size of RKK-108, which has higher molecular weight than RKK-43 may be due to the higher amount of PEG protecting the alkyl groups from intermolecular association. RKK-153 which has similar molecular characteristics compared to RKK-108 except that it has higher alkyl content has hydrodynamic radii of 15 and 25 nm at 1 mg/ml and 5 mg/ml concentrations respectively. Lower Rh values could be due to the predominance of intramolecular association over intermolecular association which is favorable in the case of RKK-153 with higher alkyl content.

Intermolecular association may be reduced by small molecular encapsulation inside the hydrophobic pocket. The measured hydrodynamic radii of 1 mg/ml solutions of RKK-43, 108 and 153 after pyrene encapsulations were found to be reduced drastically to 8, 10 and 14 nm respectively. This may be due to hydrophilic corona of PEG chains collapsing around the pyrene molecules embedded inside the hydrophobic pocket formed by the intra molecular association of alkyl chains.

Synthesis of Sulfonic Acid Group Containing Polymers 100 mg KH was weighed in to a 100 ml round bottom flask containing 10 ml anhydrous THF. To this a solution of RKK-108 (2 g) dissolved in 125 ml anhydrous THF was added. The mixture was stirred for 45 minutes after which a solution of 1,3-propane sultone (30 mg) in 10 ml anhydrous THF was added. The mixture was stirred for additional 12 hours. THF was evaporated and the polymer was dissolved in water and acidified to neutral pH. The final polymer was purified by dialysis. Proton NMR showed the presence of 2.5% sulfonic acid groups. The amount of sulfonic acid groups can be varied by changing the amount of 1,3-propane sultone added.

Fatty Acid Binding

One of the major functions of HSA is the binding and transport of fatty acids. The fatty acid binding properties of these polymers can be studied by $^{13}C$ NMR spectroscopy according to several reports which contain NMR studies of fatty acid binding with proteins. The basis of interaction studies by $^{13}C$ NMR spectroscopy is that the chemical shift of the carbons of the fatty acid in the bound and free form differ. Alternative approaches may include titration calorimetry.

Proton-decoupled $^{13}C$ NMR spectra were recorded on a Bruker™ (75.47 MHz for carbon) NMR spectrometer. Samples were dissolved in water and locking was done using $CD_3OD$ in a capillary tube inserted into the sample. The multiplet at 49.15 from $CD_3OD$ was used as an internal reference. Potassium salt of $[1-^{13}C]$ palmitic acid (PA) was synthesized following a reported procedure. Initially spectra were recorded at concentrations above and below the critical micelle concentration (CMC) to see the association effects. 1.6 mM is the CMC of potassium palmitate (KPA). The resonances of enriched carboxyl carbon appeared at 184.37 and 184.12 respectively. This agrees well with a reported value of 184.2 ppm.

The results in Table 3 show that KPA binds to polymer RKK-43 (HPG, 2.5% C18 chains, 21% MPEG; Mn=44,000) as evidenced by the chemical shift of the carboxylate carbon. Both these and the pure KRA results show the chemical shift is insensitive to the presumed formation of micelles since shifts were similar above and below the CMC. For core HPG (RKK-7) or HPG-MPEG without octadecyl chains (RKK-99) the shift was similar to free palmitate. This indicates that the potassium palmitate is bound in a hydrophobic environment, which leads to the upfield shift of the carboxylate resonance.

To obtain comparative data for various polymers, 35 mg of selected polymers were dissolved in 0.5 ml of 1.5 mM KPA and the change in chemical shift determined (Table 3). It was found that the change in chemical shift was significant only for polymers containing hydrophobic groups and depended weakly on the amount of alkyl group incorporated. Polymers with Brij-76 groups also bound potassium palmitate efficiently.

The stoichiometry of the complex between KPA and RKK43 was determined by a mole ratio method. The concentration of palmitate was kept constant at 1.5 mM, which is below its CMC and the molar concentration of RKK-43 (Mn=45,000) was varied from 0.16 to 3 mM. A plot of the change in chemical shift, $\Delta\delta$, as a function of polymer concentration resulted in two lines intersecting at an approximate ratio of 3:1, indicating about 3 moles of KPA bound per mole of RKK-43.

Solubilization properties were considered using 200 mg each of RKK-43, RKK-108, RKK-153, RKK-99 and RKK-7, dissolved in 1 mL of water and stirred with 20 mg of palmitic acid for two days. The resulting solutions were filtered twice through a 0.22 μm filter membrane and analyzed by $^{13}C$ NMR. An intense peak appeared at around 177 ppm in the case of RKK-43, RKK-153 and RKK-108, which are copolymers containing octadecyl chains, whereas no such peak appeared in the cases of RKK-7 and RKK-99 which contained no alkyl groups. The peak at 177 ppm corresponded to the enriched carboxyl carbon of palmitic acid.

For quantitative estimation of the palmitic acid solubilized by the above polymers, filtered solutions of RKK-108 (10 and 20 wt %)-palmitic acid mixtures were freeze dried and the residue were dissolved. $^{13}C$ NMR was taken in 100 mM chromium(III)triacetylacetonate (relaxation agent) solution in methanol-d4. Good signal to noise ratios were obtained with a pulse delay of one second using inverse gated decoupling without nuclear overhauser enhancement (NOE). On average, a single polymer molecule of RKK-108 with 9.5 octadecyl chains dissolved 0.75 molecule of palmitic acid. RKK-153, which has similar molecular weight and composition except that it contains 1.5 octadecyl chains in a single polymer chain, was found to solubilize 2.8 molecules of palmitic acid. The validation was performed using the obtained NMR data of a known mixture of $[1-^{13}C]$ palmitic acid and RKK-108.

RKK-259 with 17% $C_{10}$ chains was found to solubilize 21 molecules of palmitic acid.

TABLE 3

The chemical shift data of the interaction between potassium palmitate (KPA) and various polymers

| Sample Code | Composition | polymer (RKK) properties | pH of the medium | Solvent | Concentration of PA (mM) | Chem. Shift of $^{13}C1$ (ppm) |
|---|---|---|---|---|---|---|
| 1 | KPA | | 10.0 | $H_2O$ | 3.00 | 184.37 |
| 2 | KPA | | 10.0 | $H_2O$ | 1.5 | 184.12 |
| 3 | KPA + RKK-43 | 2.5 mol % ODE, 21% PEG | 7.0 | $H_2O$ | 1.5 | 182.64 |
| 4 | KPA + RKK-99 | No alkyl gps, 37% PEG | 7.0 | $H_2O$ | 3.00 | 183.56 |
| 5 | PA + RKK-7 | Polyglycidol | 7.0 | $H_2O$ | 0.49 | 183.81 |
| 6 | KPA + 55 | 1.73 mol % ODE, 24% PEG | 7.0 | $H_2O$ | 1.5 | 182.78 |
| 7 | KPA + 52 | 5.9 mol % ODE, 31% PEG | 7.0 | $H_2O$ | 1.5 | 182.49 |
| 8 | KPA + 72 | 2.76 mol % brij, 14% PEG | 7.0 | $H_2O$ | 1.5 | 182.46 |
| 9 | KPA + 85 | 6.25 mol % brij, 13.5% PEG | 7.0 | $H_2O$ | 1.5 | 182.36 |
| 10 | KPA + 77 | 13 mol % brij, 8% PEG | 7.0 | $H_2O$ | 1.5 | 182.34 |
| 11 | KPA + 122 | 3 mol % GHDE, 34% PEG | 7.0 | $H_2O$ | 1.5 | 182.54 |
| 12 | KPA + 120 | 5.8 mol % GNPE, 21% PEG | 7.0 | $H_2O$ | 1.5 | 182.60 |
| 13 | KPA + 117 | 10 mol % PGE, 30% PEG | 7.0 | $H_2O$ | 1.5 | 183.18 |
| 14 | KPA + 108 | 2.6 mol % ODE, 40% PEG | 7.0 | $H_2O$ | 1.5 | 182.66 |
| 15 | KPA + 110 | 0.8 mol % ODE, 18% PEG | 7.0 | $H_2O$ | 1.5 | 182.67 |
| 16 | KPA + 153 | 4.6 mol % ODE, 40% PEG | 7.0 | $H_2O$ | 1.5 | 182.56 |

Bilirubin Binding

One of the major ligands for albumin is bilirubin. The binding is through both hydrophobic and electrostatic interactions. To mimic the bilirubin properties of albumin, HPGs having both amine and alkyl groups were prepared by the following method. Low bilirubin binding capacities were obtained for HPGs containing hydrophobic (alkyl) modification alone, whereas binding capacities close to that of albumin (1 to 2 BR molecules per molecule) was achieved through the amine modification.

A three neck round bottom flask was used for the polymerization reactions. One neck was connected to an argon inlet and another closed with a stopper. The third neck was closed with a rubber septum and was used for monomer addition. Initially the flask was flushed with argon and a weighed amount of trimethyloyl propane (120 mg) was added to it. Required volume of potassium methylate (100 µL) solution in methanol was then added to it and the mixture was stirred for 15 minutes. The flask was kept in an oil bath at 95° C. and the excess methanol was evaporated in vacuum with stirring. After this, the mechanical stirrer was connected to replace the stopper. A mixture of glycidol (5.4 mL) and N-(2,3-epoxypropyl)phthalimide (1.64 g) was added drop wise to the reaction flask using a syringe pump. As the reaction progressed the mixture became viscous, however, the mechanical stirrer was able to mix it efficiently. After complete addition, the reaction mixture was stirred for additional 5 hours. MPEG-epoxide (15 mL) was then added slowly using the syringe pump in 12 hours time. The whole mixture was then stirred for additional 5 hours. The polymer was dialyzed against water using a dialysis membrane (1000 MW CO). The dry polymer was obtained after freeze drying. According to NMR, 6.7% of phthalimide and 25% MPEG groups were present in the obtained copolymer. Phthalimide groups were converted to amine groups by hydrazinolysis. Hydrazine monohydrate (2.8 ml) was added to the solution of the polymer in methanol and the mixture was refluxed for 16 hours. After cooling, the mixture was filtered, methanol was evaporated. The obtained polymer was dissolved in water and was subjected to dialysis. After drying, 14.5 g of a colorless, highly viscous polymer was obtained. The 1H NMR showed the absence of phthalimide peaks. The dialysed copolymer (1 g) was dissolved in 10 ml methanol and 0.5 g of octadeceneepoxide (ODE) was added. The reaction mixture was stirred at 65° C. for 1.5 days. After completion of the reaction, excess of ODE was extracted with hexane, and methanol was evaporated to get the final polymer. The amine and the alkyl contents have been varied by employing different amounts of phthalimide and alkene epoxides of different chain lengths.

Drug Carrying Capacity

"Unimolecular micelles" having a hydrophobic core and hydrophilic shell are known to solubilize hydrophobic molecules such as pyrene in water. Tests using pyrene as the binding molecule and RKK408, RKK-43 and RKK453 (10 wt % solutions) as the host polymers were carried out. The filtered solutions were freeze dried and redissolved in $D_2O$. The solutions were analyzed by $^1H$ NMR and showed the presence of aromatic protons corresponding to pyrene. 0.39, 0.40 and 1.4 moles of pyrene per mole of polymer respectively were found to be solubilized. This confirms that the polymers of this invention can also be used for entrapping hydrophobic drugs for controlled delivery because the copolymers with hydrophobic groups bind external hydrophobic molecules in water. A possible mechanism is that the alkyl chains coupled to HPG arrange themselves inside the molecule into a hydrophobic core resembling the interior of a micelle formed in water by hydrophobic association of alkyl chains. Association of hydrophobic external molecules may then occur by partition of the external materials into the core where they are dissolved.

Amphiphilic polymers are known to form intermolecular associations through their hydrophobic groups and some will also bind fatty acids or hydrophobic molecules such as pyrene. However, these types of molecules do not necessarily form simple micelles at a single concentration because of the large size of the hydrophilic head groups. As the concentration in water increases, the extent of association may also increase which can allow the amount of pyrene bound to rise faster than the polymer concentration. Pyrene solubilities in aqueous solutions of various concentrations of RKK-43, RKK-108 and RKK-153 were therefore measured using UV/VIS spectroscopy. An excess of pyrene was stirred with the polymer solutions of various concentrations for 15 hours, filtered using 0.2 µM syringe filters and the resultant solution analyzed. Literature value of 29,500 for $\in_{max}$ was used for concentration measurements. In water the solubility of pyrene is very low at room temperature and is $7\times10^{-7}$ M. The solubility increases in the presence of polymers and the value increases with increase in polymer concentration. Plots of solubility against polymer concentrations were linear indicating the absence of any associations in the concentration range studied, as any association behavior would lead to a change in slope. The slopes of the fitted straight lines showed that a single molecule of polymer RKK-43, RKK-108 and RKK-153 dissolves 0.35, 0.41 and 1.32 molecules of pyrene. The higher solubility in the case of RKK-153 might be due to higher alkyl content in a single polymer chain which shows solubilizing ability even at concentrations as low as $1.25\times10^{-6}$ mol (Table 2). The values obtained for all these polymers are very close to that obtained from proton NMR. Addition of salt like NaCl increases the pyrene solubilization significantly. This may be due to the decrease in the concentration of water inside the hydrophobic environment thereby increasing its hydrophobicity.

Fluorescent probes can be used for quantitative analysis of a polymer molecule's binding capacity which is important for formulating drug delivery vehicles. We used anionic fluorescent probe (1-anilinonapththalene-8-sulfonic acid (ANS) for this purpose. Phosphate buffered saline (PBS: 150 mmol/L NaCl, 1.9 mmol/L $NaH_2PO4$, 8.1 mmol/L $Na_2HPO4$, pH 7.4) was used to prepare the solutions. The excitation wavelength was set at 370 nm and the emission range was set between 400 and 600 mu. Spectra were recorded using a plate reader.

Pure ANS in water has weak fluorescence in a range 400-600 with a maximum at 520 nm. This is because of its low fluorescence yield in a polar environment. Addition of RKK polymer leads to increase in fluorescence intensity and the blue shift of the emission maximum ($\lambda_{max}$), typically from 520 nm to 475 nm. Since the RKK polymer solution do not show any peak in the range, the change in spectrum is considered to be due to the binding of ANS by RKK polymers. The enhancement of fluorescence yield and a blue shift upon addition of RKK polymers suggest that ANS aromatic rings are placed in less hydrophilic environment.

The binding constant (Kb) and the number of binding centers per one molecule (n) for RKK polymers were determined by the double fluorometric titration technique. In the first fluorometric titration, increasing concentrations of RKK polymers were added to constant concentration of ANS and the extreme intensity of ANS fluorescence was measured. In the second fluorometric titration increasing concentrations of ANS (CANS) were added to constant concentration of RKK polymer and the fluorescence intensity was measured. Plot of $C_{pol}/C^{ANSbound}$ against $1/C_{free\,ANS}$ and linear regression gave the values for Kb and n. RKK-153, 108, 117 were used for the study and the values are given in Table 4.

TABLE 4

ANS binding by RKK polymers

| Polymer | Mol/Mol polymer | Binding constant × $10^{-5}$ mol$^{-1}$ |
|---|---|---|
| RKK-108 | 0.32 | 2.4 |
| RKK-153 | 0.60 | 4.5 |
| RKK-117 | 0.26 | 4.1 |
| HSA | 1.82 | 11 |

RKK-153 with higher alkyl content was found to bind more ANS molecules than RKK-108 and has a higher binding constant. While these values are lower than that reported for human serum albumin, it is to be noted that HSA has specific hydrophobic pockets containing cationic groups. New modifications to make use of both electrostatic and hydrophobic forces will enhance the interaction between the polymer and ANS.

The above described results with small molecule binding shows that HPG polymers with internal hydrophobic pockets are useful as carrier molecules and drug delivery vehicles in biomedical applications.

Animal Testing

Animal trials were carried out under contract with the Advanced Therapeutics group at the B.C. Cancer Research Centre on the Vancouver Hospital site (Vancouver, British Columbia, Canada). Initially toxicology studies were conducted for the polyglycidol core material. Three HPG compounds were tested in mice, designated in Table 1 as RKK-1 ($M_n$=4,250), RKK-7 ($M_n$=15,400) and RKK-11 ($M_n$=112,000). They were injected into Balb C mice at four concentrations (dosages) from 100 mg/ml (1 g/Kg) to 6.25 mg/ml (62.5 mg/Kg), 2 mice per concentration per compound, and followed for 28 days for signs of toxicity (e.g., lethargy, dry eyes, weight loss, scruffy coats). No untoward indicators were found and all animals, even those with the very high doses of the highest molecular weight compound, grew normally with no signs of toxicity. Hence, the core HPG compound was well tolerated by mice.

The copolymers RKK-43, RKK-108 and RKK-117 dissolved in isotonic saline were also tested in Balb/c mice following intravenous administration at concentrations 0.5 g/Kg and 1 g/Kg and followed for 30 days for signs of toxicity and body weight loss. No signs of toxicity or weight loss were observed even in the case of RKK-117 which contains 10% aromatic groups.

Pharmacokinetics

Pharmacokinetic analyses of RKK-43 and RKK-108 were conducted after tritium labeling to assess their circulation longevity and organ uptake. Radiolabeling was done by partial methylation of about 1% of the hydroxyl groups. First, approximately 5% of the hydroxyl groups were converted into potassium alkoxides by reaction with potassium hydride and then reacted with tritium labeled methyl iodide ($C^3H_3I$). The products were purified by dialysis. Mice were injected at a dose of 1 g/Kg and blood was analyzed at 30 min, 1, 2, 4, 24, 48 and 72 hours, 7, 14 and 30 days. Plasma was assessed for levels of test compounds by scintillation counting.

It was found that concentrations of RKK-43 in plasma were reduced to 50% of initial dose after 24 hours. The levels decreased to less than 1% after 7 days. In the case of RKK-108 the levels were 75% after 24 hours. This may be due to its higher molecular weight (larger size) as well as higher incorporation of PEG. Molecular weight dependence of polymer elimination from blood circulation has been reported. Since these polymers are chemically constituted of only —C—C— and C—O—C bonds (neither of which are substrates for common enzymes in the circulation) rapid enzymatic breakdown does not occur.

The levels of RKK polymers in plasma was analyzed as a function of time using a standard two-compartment open model consisting of a central compartment (B) which is mainly plasma, and the tissue compartment (T). The elimination part is represented by compartment C. The central compartment is considered open since elimination occurs from this compartment by excretion. There is assumed to be reversible exchange between the blood and tissue compartments. This two compartment open model is described in more detail below with $k_{12}$ and $k_{21}$ representing rate constants for transfer between compartments 1 and 2, the plasma and tissues and $k_2$ is the rate constant for elimination.

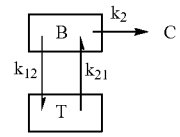

When the polymer solutions are injected intravenously into mice, the polymer molecules will undergo simultaneous elimination and distribution processes which includes reversible diffusion into the tissues. The polymer concentration in plasma decreases with time in two distinguishable exponential phases. During the distribution phase the concentration of polymer increases to a maximum in the tissue compartment and the concentration in the blood decreases due to loss to tissue and elimination. During the elimination phase the concentration decreases both in tissue and blood compartments as a function of time. Such a system can be expressed by the equation $P(t)=Ae^{-\alpha t}+Be^{-\beta t}$ where P is the concentration of drug in plasma and t is time. Curve fitting of the data gave t=0 values for the plasma concentration of the material associated with the distribution and elimination phases (A and B) and the values for α and β. The apparent rate constants $k_{12}$, $k_{21}$, and $k_2$ are calculated using the following equations and the calculated values are shown in Table 5.

$$P_0 = A + B$$

$$k_{21} = (A\beta + B\alpha)/P_0$$

$$k_2 = \alpha\beta/k_{21}$$

$$k_{12} = \alpha + \beta - k_2 - k_{21}$$

TABLE 5

Rate constants determined from pharmacokinetic analysis of polymer concentrations in plasma over time

| Polymer | A (mg/mL plasma) | B (mg/mL plasma) | α (h$^{-1}$) | β (h$^{-1}$) | P$_0$ | k$_{21}$ (h$^{-1}$) | k$_2$ (h$^{-1}$) | k$_{12}$ (h$^{-1}$) |
|---|---|---|---|---|---|---|---|---|
| RKK-108 | 8.450 | 0.220 | 0.021 | 0.00149 | 8.670 | 0.00198 | 0.01558 | 0.00459 |
| RKK-43 | 8.123 | 0.040 | 0.028 | 0.00050 | 8.163 | 0.00064 | 0.02218 | 0.00589 |

The low molecular weight RKK-43 was eliminated from the system one and half times faster than high molecular weight RKK408. Its diffusion from blood to tissues is faster whereas the reverse process is slower compared to that of RKK-108. This shows that it is possible to adjust retention time in blood by manipulating the molecular weight and/or PEG content of the polymer.

At termination, various organs (liver, spleen, lungs, and heart) were collected and processed for scintillation counting and determination of test compound levels. Levels of the polymers in the organs were analyzed and the amount of polymer in the plasma present in the tissues subtracted. Values for plasma volumes in various organ tissues of mice were taken from the literature. We found that the levels of polymer detected in the organs was mainly due to the blood present, in which the concentration of polymer is relatively high. Levels of both polymers were found to increase slowly in the spleens of the mince over the 30 days of experiment, with values ranging from 0.2 to 0.4 mg per gram tissue. Levels in lungs were very low but 0.1 and 0.2 mg/g tissue levels were observed on the 14$^{th}$ day. Constant levels of RKK-43 (0.1 mg/g) were found in the heart over the period of 30 days while it was found to increase slowly from 0.03 to 0.17 in the case of RKK-108. The highest tissue levels of RKK-43 and RKK-108 were observed in the livers, with levels being around 1.6 mg/g after two days. Higher amounts of low molecular weight RKK-43 containing 20% of PEG was accumulated in the liver compared to RKK-108 which contains 40% PEG. This clearly shows the protective nature of PEG chains against uptake by the reticuloendothelial system.

This analysis indicated that the half life of RKK-108 is about 33 hr, meaning that its concentration in plasma has dropped to half its initial value over that period. This is consistent with the time periods required for postoperative support in many cases.

Coagulation

Three polymer samples were tested for blood compatibility using the activated partial thromboplastin time (APTT) and the prothrombin time (PT) in fresh human plasma. PT is used to evaluate the extrinsic and common coagulation pathway and the results are expressed in seconds required for a fibrin clot to form after tissue thromboplastin (innovin) has been added to the blood sample. APTT is used to evaluate the intrinsic and common coagulation pathway. The results are expressed in seconds required for a fibrin clot to form in the plasma sample after a partial thromboplastin reagent (actin) and calcium chloride have been added to the sample. Blood was mixed with a measured amount of citrate and the plasma was obtained by centrifugation.

RKK-1, which is core HPG, slightly decreased the prothrombin time and increased the activated partial thromboplastin time considerably with increasing concentration. RKK-111, which is a copolymer of glycidol, epoxide of Brij-76 and PEG-epoxide increased PT and APTT with increasing concentration. However, RKK-108, which is a copolymer of glycidol, octadecene epoxide and PEG epoxide, did not affect the APTT and PT even if present at high concentration (10 wt %). Hence, MPEG may be used to shield the HPG and hydrophobic core from coagulation proteins.

Red Cell Aggregation and Blood Rheology

The apparent viscosity of anticoagulated whole blood depends mainly on plasma viscosity, hematocrit, the geometry and deformability of red blood cells (RBC) and their aggregation. Blood viscosity at high shear rate reflects red blood cell deformability and the viscosity at low shear rate reflects erythrocyte aggregation. Erythrocytes aggregate naturally in the presence of macromolecules like immunoglobulins, fibrinogen or high molecular weight dextran, forming primarily linear aggregates known as rouleaux. Extreme versions of these aggregates can be very difficult to break down in flow due to reversible bridge formation by the polymeric molecules which adsorb between the erythrocytes. On the other hand, red cells do not aggregate in the presence of albumin or low molecular weight dextran (≤40,000) which do not form the bridges due to their smaller size and weaker adsorption. Red cell aggregation increases whole blood viscosity and presents a challenge to the heart and circulatory system of patients already compromised by their medical condition.

The response of red cells to HPG derivatives added to human blood in vitro was determined by microscopic examination and whole blood viscometry. Derivatives were prepared in isotonic saline at 100 mg/mL and were filtered on 0.20 μm filters. These were added to freshly drawn, EDTA anti-coagulated blood to a final plasma concentration of 17.2 g/L. The resulting plasma concentration was 82.8% of the native value. The hematocrits were between 39 and 43% v/v.

Under microscopic examination aggregation was assessed using a qualitative index that scales with the strength of cell-to-cell interaction.[31] The visual aggregation index (VAI) scale is:

| VAI | | |
|---|---|---|
| | 0 | single cells, no aggregation |
| | 1 | 50% single cells: 50% aggregated cells |
| | 2 | rouleaux: >90% cells in aggregates |
| | 2.5 | rouleaux: cap-ends, side-to-side aggregates |
| | 3 | clumps: distorted cells & rouleaux |

Compared to control, the HPG core and polymers with >35% MPEG, whether or not they contained octadecyl chains, had no significant effect on aggregation at 17 mg/mi. However, polymers with (a) lower MPEG content (RKK-43: 21%), (b) higher molecular weight MPEG chains (28% MPEG 550 cf MPEG 350 used for all other derivatives) and (c) a polymer containing Brij rather than C18 and MPEG chains, all produced significantly elevated red cell aggregation.

Whole blood viscosity of blood-derivative mixtures were determined at 35±1° C. in a Contraves LS2™ rotational Couette viscometer. Shear stress was measured at a series of shear rates between 0.2 and 80 s$^{-1}$. Whole blood variable shear rate viscometry studies showed that RKK-43 (2.5% C18, 21% MPEG) significantly elevated low shear rate viscosity while RKK-108 (2.6% C18, 38% MPEG) had little effect, consistent with results of the aggregation studies. This shows that use of a high concentration of PEG chains helps to protect the HPG/hydrophobic core from binding to cell surfaces It is to be noted that all the synthetic plasma expanders in current use cause increased whole blood viscosity at low shear rate, indicative of increased red blood aggregation.

Complement Activation

When a foreign material comes in contact with blood, the host defense system called complement system which comprises more than 20 plasma proteins activates and a series of chemical reactions take place leading to inflammation. There are two pathways of activation: the classical and the alternative pathways. The classical pathway is activated by an antigen-antibody complex and the alternate pathway requires only a foreign material. Examples of polymers known to cause complement activation include dextran, regenerated cellulose, sephadex, nylon, poly(methylmethacrylate), poly(propylene), poly(acrylamide), poly(hydroxyethylmethacrylate), plasticised PVC. An example of polymer which thought to not activate complement is poly(N-vinylpyrrolidone). Surface induced complement activation has been reported to activate cell adhesion, platelet aggregation and platelet activation leading to thrombosis. Since the activation peptide C3a is formed during both the activation pathways, its estimation leads to an accurate indication of the complement activation.

The effects of HPG polymers on complement activation were studied in vitro by measuring C3a in citrate anticoagulated plasma using QUIDEL™ Complement C3a Enzyme Immunoassay following the procedure mentioned in the kit. The plasma collected from four healthy volunteers were pooled and was mixed with polymer solutions in 1:1 volume ratios, incubated at 37° C. for 2 hours and frozen at −80° C. until analysis. The results are shown in Table 6. Known biocompatible polymers including PEG, dextran, hetastarch, poly(N-vinylpyrrolidone) were tested for comparison. The C3a levels generated in the case of branched polyglycidol(RKK-1) and linear glycidol (RKK-213) were similar to that of control experiment in which the incubation was done in the presence of saline solution alone. This shows that these polymers are non complement activating and therefore biocompatible. Among the other polymers tested, the C3a levels were similar to the controls in the case of PEG and dextran whereas higher C3a generation was observed in the case of hetastarch and poly(N-vinylpyrrolidone). Among the derivatized polyglycidols, RKK-108 was found to be non complement activating whereas slightly higher values were obtained in the case of RKK-153.

TABLE 6

Complement activation by RKK polymers

| Polymer Code | Composition | C3a ng/mL |
|---|---|---|
| Saline control | | 13160 |
| PEG - 350 | | 10847 |
| Dextran 23K | | 15216 |
| Hetastarch | | 25236 |
| PVP | | 19888 |
| RKK-1 | Branched polyglycidol | 14144 |

TABLE 6-continued

Complement activation by RKK polymers

| Polymer Code | Composition | C3a ng/mL |
|---|---|---|
| RKK-213 | Linear polyglycidol | 13392 |
| RKK-108 | PEG/ODE/PEG | 14592 |
| RKK-153 | PEG/ODE/PEG | 17992 |

Polymer Con. = 2 wt %; Inc. Temp = 37° C.; Incubation time 120 min; polymer solution was prepared in isotonic saline solution (150 mM), PEG = polyethyleneglycol; ODE = octadecene epoxide)

The alternative pathway of complement activation is reported to begin with the reaction of nucleophiles such as amino and hydroxyl groups with a labile thioester group on the C3b molecule. The hyperbranched polyglycidol core molecule has a number of hydroxyl groups which equals the degree of polymerization. However, as demonstrated above, these polymers are surprisingly non complement activating in plasma.

The effect of Brij-containing molecules on red cell aggregation may be due to the structure of the end group caps, where the PEG chains are coupled to the HPG end groups with the alkyl chain forming the new end groups. This may allow molecular and cellular aggregation to occur. Thus, the opposite orientation with PEG chains as the end groups would be better or the PEG caps should be added after the alkyl groups, as described above.

Platelet Activation

To measure platelet activation, blood was collected from normal donors into sodium citrate anticoagulant and the platelet rich plasma (PRP) isolated by centrifugation. Fifty microliters of PRP was then incubated at 37° C. with an equal volume of polymer suspended in saline at concentrations ranging from 0.5-2 wt. %. Aliquots of the incubation were removed at 10, 30 and 100 minutes to assess the activation state of the platelets using fluorescence flow cytometry. Expression of the platelet activation marker CD62P and the platelet pan-marker CD42 were detected using a Coulter Epics-XL™ (Miami, Fla.) and a double staining method. Briefly, 10 μL of post-incubation polymer/platelet mix was diluted in HEPES buffer and incubated with 5 μL of monoclonal anti-CD42-FITC and 5 μL of monoclonal anti-CD62P-PE (both from Immunotech, Marseilles, France). The addition of 1 U/mL of bovine thrombin (Sigma) was used to activate platelets as a positive control. Mouse IgGs conjugated to the same chromophore (FITC or PE) were used as the non-specific binding controls. After 30 min incubation, the samples were fixed with 1 mL of formol saline. Samples were analysed within 2 hours; instrument gates were sent to count 5000 platelets as defined by their forward scatter profile. Data are reported as the percentage of platelets positive for both of the bound antibodies (Table 7).

Platelets exposed to thrombin (positive controls) showed an anticipated rapid increase in CD62 expression within 10 minutes to 88.7% of cells analyzed. Platelets exposed to saline alone had a maximum of 24.8% CD62 expression at 100 minutes while polymers known to be biocompatible, PEG 350, hetastarch, PVP and dextran, caused CD62 expression at levels ranging from 12.2 to 23.8% (see table 7). All RKK compounds tested at up to 2 wt % caused ≤25%, platelet activation expression, indicating that these compounds have little or no direct effect on platelets and the activation levels are consistent with those seen with compounds that are already in human use. Although there was some CD62 expression seen in all samples other than those incubated only with the control antibodies (0.06%), the polymer induced activation was no greater than that seen with saline alone; thus, the low level CD62 expression seen in these studies can be attributed to the choice of suspending medium for the polymer.

TABLE 7

Platelet activation data

| Polymer | Conc. Wt % | Incubation time (min) | | |
|---|---|---|---|---|
| | | 10 | 30 | 100 |
| Negative control | | 0.06 | | |
| Positive control | | 88.7 | | |
| saline | | 18.1 | 22.7 | 24.8 |
| PEG-350 | 2 | 19 | 19.9 | |
| | 1 | 14.1 | 17.1 | 14.6 |
| Hetastarch | 2 | 18.8 | 21.2 | |
| | 1 | 13 | 23.8 | 17.3 |
| PVP | 2 | 14.1 | 15.9 | |
| | 1 | 11.2 | 15.9 | 16.2 |
| Dextran | 2 | 12.2 | 16.1 | |
| | 1 | 12.6 | 18.4 | 17.1 |
| RKK-28 | 2 | 13.3 | 18.2 | |
| | 1 | 14.1 | 21.5 | 17 |
| | 0.5 | 14 | 18.4 | 22.4 |
| RKK-108 | 2 | 7.44 | 9.4 | |
| | 1 | 11.3 | 16.4 | 15 |
| | 0.5 | 13.5 | 17.9 | 15.1 |
| RKK-153 | 2 | 3.3 | 3.6 | |
| | 1 | 8.4 | 11.3 | 19.3 |
| | 0.5 | 13.1 | 14.7 | 15.1 |
| RKK-43 | 2 | 6.14 | 4.8 | |
| | 1 | 11.4 | 13.3 | 21.3 |
| | 0.5 | 22.7 | 21.4 | |
| RKK-213 | 2 | 21 | 25 | |
| | 1 | 17 | 21.2 | 21.6 |
| | 0.5 | 15.2 | 21.4 | |

Plasma Protein Precipitation

It is known that addition of PEG to plasma can cause protein precipitation. This depends on PEG concentration and its molecular weight. RKK-1, RKK-108 and RKK-153 did not cause plasma protein precipitation when solutions of these polymers in 150 mM aqueous NaCl solution were added to anticoagulated plasma. No visual evidence of precipitation was observed when 100 μL of polymer solutions of various concentrations were added to 1 mL of plasma to final concentrations of 10 to 60 mg/mL. Similar results were obtained in the case of PEG-350. However protein precipitation was observed when PEG-6000 was added to a concentration of 60 mg/ml. In the case of PEG-350, plasma concentration of 180 mg/ml was needed for protein precipitation. Therefore, the RKK polymers do not cause protein precipitation when present in plasma in a concentration range where these polymers may be used as plasma expanders.

In some cases, increasing the molecular weight of the PEG would be contraindicated, as would too low a concentration of lower MW PEG. The prolonged retention of RKK-108 in the plasma of mice and the lower levels found in liver compared to RKK-43 suggest that about 40% PEG-350 chains would be ideal in some embodiments. However, the invention permits a wide range of variables while still providing for improved performance.

Acute Response to Isovolemic Blood Exchange Using Polymer RKK 108

In this study, the animals were Lewis rats of 325-360 g weight. The following solutions were used: lactated Ringers solution (control); 10 μM IC-41 (MW 83,000) prepared in lactated Ringers solution for blood exchange=15% total volume exchange (TVE). % TVE calculated according to weight=%×58 ml/kg weight of animal.

The animals were anaesthetized using 4% isofluorane and maintained at 0.5%-2% during the surgical observation period of 3 hours. The $O_2$ saturation values and the heart rate (HR) were continuously monitored using an oxymeter (Nonin™) clipped on to one of the animal's paws. Catheters made of polyethylene tubing (Clay Adams PE 50™) were inserted into each of the femoral artery and vein and were held in place with #5 silk suture. The heparinized (30 UI/mL) femoral artery catheter was hooked up to a pressure transducer (AD Instrument) through a stopcock. The pulse pressure (PP) and HR were obtained at the start of blood exchange, periodically after the early part of the exchange, at 1.5 hours into the blood exchange, and at the end of blood exchange (approx. 3 hours post-infusion).

For the control animal (n=1) (for pre-exchange blood status), blood was sampled immediately after cannulation from the femoral artery catheter: 150 μL for complete blood count (CBC); 300 μL for blood gases; 600 μL for kidney/liver function tests. The blood samples for blood gases and kidney/liver function tests were immediately brought to St Paul's Hospital Clinical Laboratory, Vancouver, Canada, for testing. The CBC analysis was conducted within 10 minutes of blood sampling. The animal was euthanized after blood collection. Organ tissues (liver, kidney, spleen, pancreas, skeletal muscle and heart) were collected for future immunohistochemical analysis.

For the experimental animal (n=1), after obtaining PP and HR readings, the respective catheters were connected to the push-pull pump (Harvard Apparatus™) where the femoral vein catheter was connected to the push 5-mL syringe (BD) while the arterial catheter was connected to the pull 5-mL syringe (via 23 gauge needles. The 15% TVE isovolemic exchange was performed at 200 μL/min. After the exchange, the animal was observed for about 3 hours while under maintenance anesthesia. At the end of 3 hours, blood samples were handled the same manner as in the control animal mentioned above. Organ tissue samples were also collected as above.

The perfusion of polymer RKK108 had minimal effects on the cardiovascular system of the animal that received the 15% total blood volume exchange (TVE) of polymer. The mean HR (335 BPM) and PP (mean of systolic/diastolic) were relatively stable and constant for the majority of the post-infusion period indicating that the polymer had little or no major effect on the ability of the heart to regulate contractility, heart rate and blood pressure at this dose. The mean PP of 77 mm Hg (approx. 96/57) in the post-infused animal displayed little fluctuations except for when the anesthetic declined in the final 30 minutes before termination.

Table 8 shows the blood cell count in the animals treated with saline or polymer, and it demonstrates little or no effect of the polymer on the major cell types in the circulation over this acute 3 hour time period. There was a possible two-fold increase in white blood cells (WBC) in the polymer treated animal that may reflect increases in the percentage of neutrophils (% N) within the population. There were also decreases in the percentage of lymphocytes (% L) in the polymer treated animals. The latter results may likely be associated with the increased time that the animals are open to surgical insult compared to the controls, and not the polymer. The immune system had sufficient time to mount a systemic response to the sites of surgical wound injury, and would increase the number of circulating WBC and/or reducing specific lymphocyte populations which could migrate to the wound site. Moreover, the polymer treated animal did have an increase in the platelet count (PLT) that appeared to still be in the normal range.

The blood chemistry data shows little or no apparent effect of the polymer on the circulating levels of red blood cells (RBC), hemoglobin (HGB), and hemotocrit (HCT). Moreover, the blood gases that were analyzed (Table 9) confirm that there is only a marginal effect of the polymer on the blood gas levels of both $pCO_2$ which and $pO_2$ as both showed little change from the control, pre-infusion values. Similarly, the net ability of the blood to buffer itself against changes in pH were not affected by infusion of the polymer as indicated by changes in pH, $cHCO_3$ (bicarbonate) and cBase as all these values were all within normal values in the polymer treated animal.

TABLE 8

Complete Blood Count

| Rat ID | Condition | WBC | % N | % L | % M | % E | % B | RBC | HGB |
|---|---|---|---|---|---|---|---|---|---|
| Lewis 3A-1 | Pre-blood exchange | 3.56 | 15.4 | 77.7 | 5 | 0.76 | 1.05 | 8.66 | 147 |
| Lewis 2B-15-1 | Post blood exchange, 15% TVE | 7.83 | 62.3 | 29.4 | 7 | .070 | 1.18 | 8.07 | 139 |

| Rat ID | Condition | HCT | MCV | MCH | MCHC | RDW | PLT | MPV | PVT | PDW |
|---|---|---|---|---|---|---|---|---|---|---|
| Lewis 3A-1 | Pre-blood exchange | 42.7 | 49.3 | 17 | 346 | 15.7 | 273 | 5.51 | 1.51 | 19.1 |
| Lewis 2B-15-1 | Post blood exchange, 15% TVE | 40.1 | 49.7 | 17.2 | 346 | 14.6 | 382 | 4.98 | 1.9 | 20.2 |

TABLE 9

Blood Gas, Oxymetry, Electrolyte and Metabolite Values

| | | Blood Gas Values | | | | | |
|---|---|---|---|---|---|---|---|
| Rat ID | Condition | pH | pCO2 mmHg | pO2 mmHg | cHCO3 (P)c mmol/L | cBase (B)c mmol/L | Barometer mmHg |
| Lewis 3A-1 | Pre-blood exchange | 7.43 | 46 | 423 | 30 | 5 | 758 |
| Lewis 2B-15-1 | Post blood exchange, 15% TVE | 7.49 | 36.8 | 464 | 28.1 | 5.2 | 757 |

| | | Oxymetry Values | | | | | |
|---|---|---|---|---|---|---|---|
| Rat ID | Condition | sO2 | ctHb g/L | Hctc | FO2Hb | FCOHb | FMetHb |
| Lewis 3A-1 | Pre-blood exchange | 0.98 | 137 | | | | |
| Lewis 2B-15-1 | Post blood exchange, 15% TVE | 0.984 | 150 | 0.459 | 0.997 | −0.001 | −0.012 |

Measurement of Osmotic Pressure

Osmotic pressure (OP) was measured using a Jupiter™ 231 membrane osmometer (UIC Inc, Joliet, Ill.). A two-layer, 5000 dalton cut-off membrane (Gonotec GMBH, Berlin) was prepared as recommended and OP was measured in water at 25° C. Human serum albumin (HSA) was measured as a control sample and the measured molecular weight is in agreement with the accepted value of 67,000 daltons.

Results for human serum albumin (HSA) and RKK-108 osmotic pressure are summarized in Table 10. The results show that at similar concentrations, RKK-108 has lower osmotic pressure than albumin. This means that a higher concentration of the polymer may be selected in order to produce a similar osmotic effect to that of albumin.

TABLE 10

Membrane Osmotic Pressure

| membrane: | 5000 Dalton cut-off |
| solvent: | water |
| temperature: | 25° C. |

| solute | concentration g/mL | pressure dynes/cm2 | Mn† g/mol | A2‡ mol-cm3/g2 |
|---|---|---|---|---|
| Human Serum Albumin | 0.0091 | 10000 | 68000 | 0.0033 |
| dHPG - (RKK-108) | 0.01 | 5500 | 53000 | 0.00033 |
| +/-(1 SD) | | 300 | 16000 | 0.00001 |

†number average molecular weight.
‡second virial coefficient

Although the foregoing invention has been described in some detail by way of illustration and example for purposes of clarity of understanding, it will be readily apparent to those of skill in the art in tight of the teachings of this invention that changes and modification may be made thereto without departing from the spirit or scope of the appended claims. All patents, patent applications and publications referred to herein are hereby incorporated by reference.

ADDITIONAL REFERENCES

1 Salmon, J. B.; Mythen, M. G. *Blood reviews* 1993, 7, 114.
2 Cochrane injury group albumin reviewers. The Cochrane Library 1998, 3.
3 Schierhout, G.; Roberts, I.; Alderson, P. The Cochrane Library 1998, 3,
4 Bunn, F.; Alderson, P.; Hawkins, V. The Cochrane Library 2000, 4.
5 Paull, J. *Anaesth. Intensive care* 1987, 15, 163.
6 Battle, J.; Del Rio, F.; Lopez Fernandez, M. F. *Throm. Haemost.* 1985, 54, 697.
7 a) Diehl, J. T.; Lester, J. L.; Cosgrove, D. M. *Ann Thorac surg.* 1982, 34, 674 b) Bremerich, D. H.; Lischke, V.; Asskali, F.; Forster, H.; Behne, M. *International Journal of Clinical Pharmacology and Therapeutics* 2000, 38, 408. C) Felfemig, M.; Franz, A.; Braunlich, P.; Fohringer, C.; Kozek-langencker, A. *Acta Anaesthesiol Scand.* 2003, 47, 70.
8 a) Treib, J.; Baron, J. F.; Grauer, M. T.; Strauss, R. G. *Intensive care med* 1999, 25, 258 b) Dintenfass, L. Rheology of blood in diagnostic and preventive medicine Butterworths, London, 1976, 181,
9 Sunder, A.; Hanselmann, R.; Frey, H.; Mulhaupt, R. *Macromolecules* 1999, 32, 4240.
10 a) Jones, M. C.; Leroux, J. C. *Eur. J. Pharmacol. Biopharm.* 1999, 48, 101. B) Kataoka, K.; Harada, A.; Nagasaki, Y. *Adv. Drug Deliv. Rev.* 2001, 47, 113. C) Kabanov, A. V.; Batrakova, E. V.; Alakhov, V. Y. *Adv. Drug Deliv. Rev.* 2002, 54, 759.
11 Kautz, H.; Sunder, A.; Frey, H. *Macromol. Symp* 2001, 163, 67.
12 Organic Synthesis CV1 494.
13 U.S. Pat. No. 6,221,977
14 Morgan, M. T.; Carnahan, M. A.; Immoos, C. E.; Ribeiro, A. A.; Finkelstein, S.; Lee, S. J.; Grinstaff, M. W. *J. Am. Chem. Soc.* 2003; 125, 15485.
15 a) Ugoloni, R.; Ragona, L.; Siletti, E.; Fogolari, F.; Visschers, R. W.; Alting, A. C.; Molinari, H. *Eur. J. Biochem.* 2001, 268, 4477, b) Stolowich, N. J.; Frolov, A.; Atshaves, B.; Murphy, E. J.; Jolly, C. A.; Billheimer, J. T.; Scott, A. I.; Schroeder, F. *Biochemistry* 1997, 36, 1719. c) Ragona, L.; Fogolari, F.; Zetta, L.; Perez, D. M.; Puyol, P.; Kruif, K. D.; Lohr, F.; Ruterjans, H.; Molinari, H. *Protein Science* 2000, 9, 1347.
16 a) Wolfrum, C.; Borchers, T.; Sacchettini, J. C.; Spener, F. *Biochemistry* 2000, 39, 1469. b) Miller, K, R.; Cistola, D, P. *Molecular and Cellular biochemistry* 1993, 123, 29. c) Cistola, D, P.; Sacchettini, J. C.; Banaszak, L, J.; Walsh, M. T.; Gordon, J. I. *J. Biol. Chem*, 1989, 15, 2700.
17 De Mul, M. N. G.; Davis, H. T.; Evans, E. E.; Bhave, A. V.; Wagner, J. R. *Langmuir* 2000, 16, 8276.
18 a) Newkome, G. R.; Yao, Z. Q.; Baker, G. R.; Gupta, V. K. *J. Org. Chem.* 1985, 50, 2004. b) Hawker, C. J.; Wooley, K. L.; Frechet, J. M. J. *J. Chem. Soc., Perkin Trans.* 1 1993, 1287.
19 Almgrem, M.; Grieser, F.; Thomas, J. K. *J. Am. Chem. Soc.* 1979, 101, 279.
20 Mackay, D. *J. Chem. Eng. Data.* 1977, 22, 273.
21 a) Liu, M.; Frechet, J. M. J. *Polym. Bull.* 1999, 43, 379. b) Shu, C.; Leu, C. *Macromolecules* 1999, 32, 100.
22 Shcharbin, D.; Klajnert, B.; Mazhul, V.; Bryszewska, M. *Journal of Fluorescence.* 2003, 13, 519.
23 a) Vladimirov, Y, A.; Dobretstoc, G. E.; (1980), *Fluorescent Probes in studying Biological Membranes*, Nauka, Moscow, Russia. B) Scatchard, G. *Ann. N. Y. Acad. Sci.* 1949, 51, 660.
24 Yamaoka, T.; Tbabata, Y.; Ikada, Y. *J. Pharrna. Sci.* 1995, 84, 349.
25 Notari, R. E. *Biopharmaceutics and Clinical Pharmacokinetics, an introduction*, 3$^{rd}$ ed., Marcel Dekker, Inc. New York, 1980
26 Bally, M. B.; Mayer, L D.; Hope. M. J.; Nayar, R. *Liposome Technol.* (Gregoriadis, G., 2$^{nd}$ ed.) CRC 1993, 3, 27.
27 Allen, T. M.; Hansen, C. *Biochim. Biophys. Acta.* 1991, 1068, 133.
28 S. Chien. *The Red Blood Cell*, D. M. Surgenor, ed., Academic Press, NY, 1975, 1031-1133.
29 Letcher R, L.; Chien, S.; Pickering, T. G.; Sealy, J. E.; Laragh, J. H. *Ame. J. Med.* 1981, 70, 1195
30 Charansonney, O.; Mouren, S.; Dufaux, J.; Duvelleroy, Vicaut, E. *Biorheology* 1993, 30, 75
31 Buxbaum, K., Evans, E., Brooks, D. E. *Biochemistry.* 1982, 21, 3225.
32 Janzen, J., Elliott, T. G., Carter, C. J. and. Brooks, D. E, *Biorheology* 2000, 37, 225.
33 Menu, P.; longrois, G.; Faivere, B.; Donner, M.; Labrude, P.; Stoltz, J. F.; Vigneron, C. *Translitsion Sci.* 1999, 20, 5.
34 a) Lamba, N, M. K.; Courtney, J. M.; Gaylor, J. D.; Lowe, G. D. O. *Biomaterials* 1999, 21, 89. b) Kidane, A, Park, K. *J Biomed Mater Res.* 1999, 48, 640, c) Lim, F.; Yu. X.;

Cooper, S. L. *Biomaterials* 1993, 14, 537 d) Payne, M. S.; Horbett, T. A. *J Biomed Mater Res.* 1987, 21, 843. e) Jantova, J.; Cheung, A. K.; Parker, C. J. *Complement and inflammation* 1991, 8, 61.
35 Beillatt, J.; Dorson, W. J. *ASAIO J.* 1984, 7, 57.
36 a) Hayashi, K.; Fukumura, H.; Yamamoto, N. *J Biomed Mater Res.* 1990, 24, 1385. b) Kamp, K. W.; Oeveren, W. V. *Int J Art Org* 1993, 16, 836
37 Chenoweth, D. E. *Artif Org* 1988, 12, 508 a) Bahulekar, R.; Tamura, N.; Ito, S.; Kodama, M. *Biomaterials* 1999, 20, 357 b) Hoenich N. A.; Woffindin, C.; Stamp, S.; Roberts, S. J.; Turnbull, J. *Biomaterials* 1997, 18, 1299 c) Crreno, M. P.; Labarre, D.; Jozefowicz, M.; Kazatchkine, M. D. *Molecular immunology* 1988, 25, 165.

We claim:

1. A hyperbranched polymer comprising a hyperbranched polyglycerol (HPG), wherein the HPG of the hyperbranched polymer has a number average molecular weight of 40,000 g/mol to 120,000 g/mol and a polydispersity of 1 to 3.5.

2. The hyperbranched polymer of claim 1, wherein the HPG has a number average molecular weight of 50,000 g/mol to 100,000 g/mol.

3. The hyperbranched polymer of claim 1, wherein the HPG has a number average molecular weight of 60,000 g/mol to 95,000 g/mol.

4. The hyperbranched polymer of claim 1, wherein the HPG has a polydispersity of 1 to 2.5.

5. The hyperbranched polymer of claim 1, further comprising one or more of polyalkyleneglycol-alkylether substituents, $C_5$ to $C_{30}$ alkyl substituents, polyalkylene glycol substituents and polyol substituents joined to alkoxide groups on the HPG.

6. The hyperbranched polymer of claim 1, wherein the hyperbranched polymer further comprises amine groups.

7. The hyperbranched polymer of claim 1, wherein the hyperbranched polymer further comprises one or more of sulfonic acid groups, phosphonic acid groups, and carboxylic acid groups.

8. The hyperbranched polymer of claim 1, further comprising at least one biologically active moiety or drug linked to the HPG or associated therewith.

9. A sterile composition comprising the hyperbranched polymer of claim 1 and at least one physiologically acceptable salt, buffer, diluent or excipient.

10. The composition of claim 9 in aqueous solution.

11. The composition of claim 10, having an intrinsic viscosity of less than 20 ml/g.

12. The hyperbranched polymer of claim 1, wherein the HPG has a number average molecular weight of 70,000 g/mol to 80,000 g/mol.

13. The hyperbranched polymer of claim 1, wherein the HPG has a polydispersity of 1 to 2.0.

14. The hyperbranched polymer of claim 1, wherein the HPG has a polydispersity of 1 to 1.7.

15. The hyperbranched polymer of claim 1, wherein the HPG has a polydispersity of 1 to 1.5.

16. The hyperbranched polymer of claim 3, wherein the HPG has a polydispersity of 1 to 1.5.

17. The hyperbranched polymer of claim 1, wherein the hyperbranched polymer comprises a branched polyether core.

18. The hyperbranched polymer of claim 17, wherein the core has a focal point derived from a polyol initiator.

19. The hyperbranched polymer of claim 1, wherein the HPG is derived from ring-opening polymerization of glycidol in the presence of an anionic initiator.

20. The hyperbranched polymer of claim 1, wherein the hyperbranched polymer further comprises regions of hydrophobicity.

21. The hyperbranched polymer of claim 20, wherein the regions of hydrophobicity are provided by the presence of aryl groups, alkyl groups, or both.

22. The hyperbranched polymer of claim 21, wherein the hyperbranched polymer comprises $C_5$ to $C_{30}$ alkyl groups.

23. The hyperbranched polymer of claim 22, wherein the alkyl groups are joined to up to 50% of alkoxide groups on the HPG.

24. The hyperbranched polymer of claim 22, wherein the alkyl groups are joined to the HPG through ether linkages.

25. The hyperbranched polymer of claim 1, wherein the hyperbranched polymer further comprises hydrophilic copolymer regions.

26. The hyperbranched polymer of claim 25, wherein the copolymer is a polyol.

27. The hyperbranched polymer of claim 26, wherein the polyol is polyglycerol.

28. The hyperbranched polymer of claim 25, wherein the copolymer is a polyalkyleneglycol.

29. The hyperbranched polymer of claim 1, wherein the polymer further comprises polyalkyleneglycol-alkylether moieties.

30. The hyperbranched polymer of claim 28, wherein the polyalkyleneglycol is a PEG.

31. The hyperbranched polymer of claim 30, wherein the PEG is an MPEG.

32. The hyperbranched polymer of claim 30, wherein the PEG has a molecular weight of from 100 to 800 daltons.

33. The hyperbranched polymer of claim 31, wherein the MPEG has a molecular weight of from 100 to 800 daltons.

34. The hyperbranched polymer of claim 32, wherein the PEG has a molecular weight of 350 daltons.

35. The hyperbranched polymer of claim 33, wherein the MPEG has a molecular weight of 350 daltons.

36. The hyperbranched polymer of claim 25 wherein the copolymers are joined to up to 80% of alkoxide groups on the HPG.

37. The hyperbranched polymer of claim 36, wherein the copolymers are joined to from 5% to 50% of alkoxide groups on the HPG.

38. The composition of claim 9, wherein the HPG of the hyperbranched polymer has a number average molecular weight of 60,000 g/mol to 95,000 g/mol and a polydispersity of 1 to 1.5.

39. The composition of claim 9, wherein the hyperbranched polymer comprises a branched polyether core.

40. The composition of claim 39, wherein the core has a focal point derived from a polyol initiator.

41. The composition of claim 9, wherein the HPG is derived from ring-opening polymerization of glycidol in the presence of an anionic initiator.

42. The composition of claim 9, wherein the hyperbranched polymer further comprises regions of hydrophobicity.

43. The composition of claim 42, wherein the regions of hydrophobicity are provided by the presence of aryl groups, alkyl groups, or both.

44. The composition of claim 43, wherein the hyperbranched polymer comprises $C_5$ to $C_{30}$ alkyl groups.

45. The composition of claim 44, wherein the alkyl groups are joined to up to 50% of alkoxide groups on the HPG.

46. The composition of claim 44, wherein the alkyl groups are joined to the HPG through ether linkages.

47. The composition of claim 9, wherein the polymer further comprises hydrophilic copolymer regions.

48. The composition of claim 47, wherein the copolymer is a polyol.

49. The composition of claim 48, wherein the polyol is polyglycerol.

50. The composition of claim 47, wherein the copolymer is a polyalkyleneglycol.

51. The composition of claim 9, wherein the hyperbranched polymer further comprises polyalkyleneglycol-alkylether moieties.

52. The composition of claim 50, wherein the polyalkyleneglycol is a PEG.

53. The composition of claim 52, wherein the PEG is an MPEG.

54. The composition of claim 52, wherein the PEG has a molecular weight of from 100 to 800 daltons.

55. The composition of claim 53, wherein the MPEG has a molecular weight of from 100 to 800 daltons.

56. The composition of claim 54, wherein the PEG has a molecular weight of 350 daltons.

57. The composition of claim 55, wherein the MPEG has a molecular weight of 350 daltons.

58. The composition of claim 47, wherein the copolymers are joined to up to 80% of alkoxide groups on the HPG.

59. The composition of claim 58, wherein the copolymers are joined to from 5% to 50% of alkoxide groups on the HPG.

60. The composition of claim 9, wherein the hyperbranched polymer further comprises amine groups.

61. The composition of claim 9, wherein the hyperbranched polymer further comprises one or more of sulfonic acid groups, phosphonic acid groups or carboxylic acid groups.

62. The composition of claim 9, further comprising at least one biologically active moiety or drug linked to the HPG or associated therewith.

63. The composition of claim 9 in dry form.

* * * * *